US007442515B2

(12) United States Patent
Ratner et al.

(10) Patent No.: US 7,442,515 B2
(45) Date of Patent: Oct. 28, 2008

(54) APPARATUS AND METHODS FOR BINDING MOLECULES AND CELLS

(75) Inventors: Buddy D. Ratner, Seattle, WA (US); Xuanhong Cheng, Seattle, WA (US); Karl Bohringer, Seattle, WA (US); Yanbing Wang, Seattle, WA (US); Yael Hanein, Tel-Aviv (IL); Ashutosh Shastry, Bellevue, WA (US)

(73) Assignee: University of Washington, Seattle, WA (US)

( * ) Notice: Subject to any disclaimer, the term of this patent is extended or adjusted under 35 U.S.C. 154(b) by 497 days.

(21) Appl. No.: 10/630,235

(22) Filed: Jul. 29, 2003

(65) Prior Publication Data

US 2004/0053334 A1    Mar. 18, 2004

Related U.S. Application Data

(60) Provisional application No. 60/399,793, filed on Jul. 30, 2002.

(51) Int. Cl.
G01N 33/53      (2006.01)

(52) U.S. Cl. ...................................... 435/7.2

(58) Field of Classification Search ............ 435/4–7.95, 435/283.1–289.1, 973; 436/514–548, 147, 436/172; 422/50–73
See application file for complete search history.

(56) References Cited

U.S. PATENT DOCUMENTS

| | | | |
|---|---|---|---|
| 5,776,748 A | 7/1998 | Singhvi et al. | |
| 5,858,687 A * | 1/1999 | Manger et al. | 435/7.21 |
| 5,976,826 A | 11/1999 | Singhvi et al. | |
| 6,368,838 B1 | 4/2002 | Singhvi et al. | |
| 6,471,761 B2 | 10/2002 | Fan et al. | |
| 6,491,061 B1 | 12/2002 | Lopez et al. | |
| 6,939,515 B2 * | 9/2005 | Carlson et al. | 422/101 |
| 7,020,355 B2 * | 3/2006 | Lahann et al. | 385/16 |

OTHER PUBLICATIONS

Takei et al. "Dynamic Contact Angle Measurement of Temperature-Responsive Surface Properties for Poly(N-isopropylacrylamide) Grafted Surfaces", Marcomolecules 1994, 27, 6163-6166.*
Achiha, K., et al., "Interactions Between Temperature-Sensitive Hydrogel Microspheres and Granulocytes," *Polymers for Advanced Technologies* 6(7):534-540, 1995.
An, Y.H., et al., "Regaining Chondrocyte Phenotype in Thermosensitive Gel Culture," *Anatomical Record* 263(4):336-341, 2001.
Aoki, T., et al., "Effect of Phenylboronic Acid Groups in Copolymers on Endothelial Cell Differentiation Into Capillary Structures," *Journal of Biomaterials Science-Polymer Edition* 9(1):1-14, 1997.
Arenkov, P., et al., "Protein Microchips: Use for Immunoassay and Enzymatic Reactions," *Analytical Biochemistry* 278(2):123-131, 2000.
Aso, Y., et al., "Thermally Controlled Protein Release From Gelatin-Dextran Hydrogels," *Radiation Physics and Chemistry* 55(2):179-183, 1999.
Badiger, M.V., et al., "Interrelation Between the Thermodynamic and Viscometric Behaviour of Aqueous Solutions of Hydrophobically Modified Ethyl Hydroxyethyl Cellulose," *Polymer* 41(4):1377-1384, 2000.
Baier, R.E., et al., "Surface Properties Determine Bioadhesive Outcomes: Methods and Results," *J. Biomed. Mater. Res.* 18(4):337-355, 1984.
Bailey, S.N., et al., "Applications of Transfected Cell Microarrays in High-Throughput Drug Discovery," *Drug Discovery Today* 7(18):S113-S118, 2002.
Benesch, J., et al., "Protein Adsorption to Oligo(Ethylene Glycol) Self-Assembled Monolayers: Experiments with Fibrinogen, Heparinized Plasma, and Serum," *J. Biomater. Sci.-Polym. Ed.* 12:581-597, 2001.
Benkhira, A., et al., "Interactions of Ethylene Oxide/Methylene Oxide Copolymers With Sodium Dodecyl Sulphate," *Polymer* 41(20):7415-7425, 2000.
Bhatia, S.N., et al., "Effect of Cell-Cell Interactions in Preservation of Cellular Phenotype: Cocultivation of Hepatocytes and Nonparenchymal Cells," *FASEB J.* 13(14):1883-1900, Nov. 1999.
Biran, I., and D.R. Walt, "Optical Imaging Fiber-Based Single Live Cell Arrays: A High-Density Cell Assay Platform," *Anal. Chem.* 74(13):3046-3054, Jul. 1, 2002.
Bohanon, T., et al., "Neural Cell Pattern Formation on Glass and Oxidized Silicon Surfaces Modified With Poly(N-Isopropylacrylamide)," *J. of Biomater. Sci. Polymer Edn.* 8(1):19-39, 1996.

(Continued)

*Primary Examiner*—Ann Y Lam
(74) *Attorney, Agent, or Firm*—Christensen O'Connor Johnson Kindness PLLC

(57) ABSTRACT

In one aspect, the present invention provides devices for binding cells or molecules, wherein each device includes (a) a body defining a first surface and a second surface that is located opposite to the first surface; (b) a heater disposed upon the first surface; and (c) a temperature-responsive layer disposed upon the second surface. In another aspect, the present invention provides methods for binding molecules or living cells to a temperature-responsive material.

46 Claims, 3 Drawing Sheets

OTHER PUBLICATIONS

Bohdanecký, M., et al., "Cloud Point Curves of Aqueous Solutions of Poly(N-Ethylmethacrylamide)," *Collection of Czechoslovak Chemical Communications* 58(10):2370-2382, Oct. 1993.

Böhringer, K.F., "Surface Modification and Modulation in Microstructures: Controlling Protein Adsorption, Monolayer Desorption and Micro-Self-Assembly," *J. Micromech. Microeng.* 13:S1-S10, 2003.

Chen, G., et al., "Effect of Protein and Cell Behavior on Pattern-Grafted Thermoresponsive Polymer," *J. Biomed. Mater. Res.* 42:38-44, 1998.

Chevillard, C., and M.A.V. Axelos, "Phase Separation of Aqueous Solution of Methylcellulose," *Colloid Polym. Sci.* 275(6):537-545, Jun. 1997.

Chiu, D.T., et al., "Patterned Deposition of Cells and Proteins Onto Surfaces by Using Three-Dimensional Microfluidic Systems," *Proc. Natl. Acad. Sci. USA* 97(6):2408-2413, Mar. 14, 2000.

Christova, D., et al., "New Thermo-Responsive Polymer Materials Based on Poly(2-Ethyl-2-Oxazoline) Segments," *Polymer* 44(8):2255-2261, 2003.

Curti, P.S., et al., "Surface Modification of Polystyrene and Poly(ethylene terephtalate) by Grafting Poly(N-Isopropylacrylamide)," *J. Mater. Sci.-Mater. Med.* 13(12):1175-1180, Dec. 2002.

d'Agostino, R., et al., (eds), *Plasma Processing of Polymers, NATO-ASI Series E: Applied Sciences vol. 346*, Kluwer Academic Publishers, Dordrecht, The Netherlands, 1996, pp. 347-363.

Dobashi, A., et al., "Control of the Solubility Transition in Novel Temperature-Responsive Linear Polymers Comprising α-Amino Acid Diamide Derivatives," *Analytical Sciences* 16(8):829-835, Aug. 2000.

Dorn, I.T., et al., "Diacetylene Chelator Lipids as Support for Immobilization and Imaging of Proteins by Atomic Force Microscopy," *Langmuir* 14(17):4386-4842, 1998.

Dworak, A., et al., "Hydrophobically Modified Polyglycidol—the Control of Lower Critical Solution Temperature," *Polymer Bulletin* 50(1-2):47-54, 2003.

Elwing, H., et al., "A Wettability Gradient Method for Studies of Macromolecular Interactions at the Liquid/Solid Interface," *J. Colloid Interface Sci.* 119(1):203-210, Sep. 1987.

Figeys, D., "Array and Lab on a Chip Technology for Protein Characterization," *Curr. Opin. Mol. Ther.* 1(16):685-694, 1999.

Folch, A., et al., "Microfabricated Elastomeric Stencils for Micropatterning Cell Cultures," *J. Biomed. Mater. Res.* 52:346-353, 2000.

Folch, A., et al., "Molding of Deep Polydimethylsiloxane Microstructures for Microfluidics and Biological Applications," *J. Biomech. Eng.-Trans. ASME* 121:28-34, Feb. 1999.

Gan, L.H., et al., "New Stimuli-Responsive Copolymers of N-Acryloyl-N'-Alkyl Piperazine and Methyl Methacrylate and Their Hydrogels," *Polymer* 42(1):65-69, 2001.

Groves, J.T., "Membrane Array Technology for Drug Discovery," *Current Opinion in Drug Discovery & Development* 5(4):606-612, 2002.

Hanein, Y., et al., "Micromachining of Non-Fouling Coatings for Bio-MEMS Applications," *Sensors and Actuators B* 81:49-54, 2001.

Hiroki, A., et al., "P-Nitrophenol Permeability and Temperature Characteristics of an Acryloyl-L-Proline Methyl Ester-Based Porous Gel Membrane," *J. of Polymer Sci. Part A: Polymer Chem.* 36(10):1495-1500, 1998.

Hirose, M., et al., "Temperature-Responsive Surface for Novel Co-Culture Systems of Hepatocytes With Endothelial Cells: 2-D Patterned and Double Layered Co-Cultures," *Yonsei Medical J.* 41(6):803-813, 2000.

Hirsch, S.G., and R.J. Spontak, "Temperature-Dependent Property Development in Hydrogels Derived From Hydroxypropylcellulose," *Polymer* 43(1):123-129, 2002.

Hong, J.S., et al., "Cloud Points and Phase Separation of Aqueous Poly(N-Vinylacetamide) Solutions in the Presence of Salts," *Colloid and Polym. Sci.* 274(11):1013-1019, Nov. 1996.

Horbett, T.A., et al., "Cell Adhesion to a Series of Hydrophilic-Hydrophobic Copolymers Studies With a Spinning Disk Apparatus," *J. Biomed. Mater. Res.* 22(5):383-404, May 1988.

Hourdet, D., et al., "Reversible Thermothickening of Aqueous Polymer Solutions," *Polymer* 35(12):2624-2630, 1994.

Idziak, I., et al., "Thermosensitivity of Aqueous Solutions of Poly(N,N-Diethylacrylamide)," *Macromolecules* 32(4):1260-1263, 1999.

Ito, Y., et al., "Patterned Immobilization of Thermoresponsive Polymer," *Langmuir* 13(10):2756-2759, 1997.

Kane, R.S., et al., "Patterning Proteins and Cells Using Soft Lithography," *Biomaterials* 20:2363-2376, 1999.

Katono, H., et al., "Thermoresponsive Swelling and Drug Release Switching of Interpenetrating Polymer Networks Composed of Poly (Acrylamide- Co-Butyl Methacrylate) and Poly (Acrylic-Acid)," *Journal of Controlled Release* 16(1-2):215-227, 1991. <http://www.sciencedirect.com/science?_ob=ArticleURL&_udi=B6T3D-475TCXK-12J&_user=10&_handle=...> [Abstract retrieved Jan. 9, 2004].

Kim, Y.D., et al., "Stable Sol-Gel Microstructured and Microfluidic Network for Patterning," *Biotechnol. Bioeng.* 73(5):331-337, Jun. 5, 2001.

Klages, C.-P., "Modification and Coating of Biomaterial Surfaces by Glow-Discharge Processes. A Review," *Mat.-wiss. u. Werkstofftech* 30:767-774, 1999.

Kubota, N., et al., "Temperature-Responsive Properties of Poly(acrylic acid-co-acrylamide)-graft-Oligo(ethylene glycol) Hydrogels," *J. of Appl. Polym. Sci.* 80:798-805, 2001.

Kudaibergenov, S.E., et al., "Temperature-Responsive Swelling and Deswelling of the Copolymers from Vinyl Ether of Ethylene Glycol and Butyl Vinyl Ether," *Macromol. Rapid Commun.* 16(11):855-860, Nov. 1995.

Kunugi, S., et al., "Microcalorimetric Study of Aqueous Solution of a Thermoresponsive Polymer Poly(N-Vinylisobutyramide) (PNVIBA)," *Polymer Journal* 34(5):383-388, May 2002.

Kushida, A., et al., "Two-Dimensional Manipulation of Differentiated Madin-Darby Canine Kidney (MDCK) Cell Sheets: The Noninvasive Harvest from Temperature-Responsive Culture Dishes and Transfer to Other Surfaces," *J. Biomed. Mater. Res.* 54(1):37-46, 2001.

Lee, B.H., et al., "A Thermosensitive Poly(Organophosphazene) Gel," *Macromolecules* 35(10):3876-3879, 2002.

Lee, R.J., and L. Huang, "Lipidic Vector Systems for Gene Transfer," *Critical Reviews in Therapeutic Drug Carrier Systems* 14(2):173-206, 1997.

Lee, W.-F., and G.-C. Hung, "Thermoreversible Hydrogels .I. Synthesis and Effect of a Hydrophobic Monomer on Swelling Behaviors of Thermoreversible Gels Prepared by Copolymerizing N-Alkoxyalkylacrylamide with Butyl Acrylate," *J. Appl. Polym. Sci.* 64(8):1477-1484, May 23, 1997.

Lin, S.-Y., et al., "Thermal Micro ATR/FT-IR Spectroscopic System for Quantitative Study of the Molecular Structure of Poly(N-Isopropylacrylamide) in Water," *Polymer* 40:2619-2624, 1999.

Loos, W., et al., "Thermo-Responsive Organic/Inorganic Hybrid Hydrogels Based on Poly(N-Vinylcaprolactam)," *Macromol. Chem. Phys.* 204(1):98-103, 2003.

Lydon, M.J., et al., "Cellular Interactions With Synthetic Polymer Surfaces in Culture," *Biomaterials* 6(6):396-402, Nov. 1985.

MacBeath, G., and S.L. Schreiber, "Printing Proteins as Microarrays for High-Throughput Function Determination," *Science* 289(5485):1760-1763, Sep. 8, 2000.

Maeda, Y., et al., "Hydration and Phase Behavior of Poly(N-Vinylcaprolactam) and Poly(N-Vinylpyrrolidone) in Water," *Macromolecules* 35(1):217-222, 2002.

Marczak, W., and A. Banaś, "The Hydrophobic and Hydrophilic Interactions in the System 2,4,6-Trimethylpyridine-Water in the Vicinity of and Above the Lower Critical Solution Temperature," *Fluid Phase Equilibria* 186(1-2):151-164, 2001.

Merrett, K., et al., "Adhesion of Corneal Epithelial Cells to Cell Adhesion Peptide Modified pHEMA Surfaces," *J. Biomater. Sci. Polymer Edn.* 12(6):647-671, 2001.

Moselhy, J., et al., "In Vitro Studies of the Interaction of Poly(NIPAm/MAA) Nanoparticles With Proteins and Cells," *J. Biomater. Sci. Polymer Edn.* 11(2):123-147, 2000.

Nakajima, K., et al., "Intact Microglia are Cultured and Non-Invasively Harvested Without Pathological Activation Using a Novel Cultured Cell Recovery Method," *Biomaterials* 22(11):1213-1223, 2001.

Nakayama, Y., and T. Matsuda, "Surface Macromolecular Microarchitecture Design: Biocompatible Surfaces via Photo-Block-Graft-Copolymerization Using N,N-Diethyldithiocarbamate," *Langmuir* 15(17):5560-5566, 1999.

Nath, N., and A. Chilkoti, "Fabrication of a Reversible Protein Array Directly From Cell Lysate Using a Stimuli-Responsive Polypeptide," *Anal. Chem.* 75(4):709-715, Feb. 15, 2003.

Ng, J.H., and L.L. Ilag, "Biomedical Applications of Protein Chips," *J. Cell. Mol. Med.* 6(3):329-340, 2002.

Okamura, H., et al., "A Novel Thermosensitive Polymer, Poly(Methyl 2-Propionamidoacrylate), With Geminal Substituents," *Polymer* 43(13):3825-3828, 2002.

Okano, T., et al., "Temperature-Responsive Poly(N-Isopropylacrylamide) as a Modulator for Alteration of Hydrophilic Hydrophobic Surface Properties to Control Activation/Inactivation of Platelets," *J. Control. Release* 36:125-133, 1995.

Pan, Y.V., et al., "Plasma Polymerized N-Isopropylacrylamide: Synthesis and Characterization of a Smart Thermally Responsive Coating," *Biomacromolecules* 2(1):32-36, 2001.

Park, S.Y., et al., "Characterization of Temperature-Induced Phase Transition of Polymer Complex Composed of Poly-(N,N-Dimethylamino)ethyl Methacrylate and Poly(Ethyacrylamide) by $^1$H-1-NMR Relaxation Time Measurement," *European Polymer Journal* 37(9):1785-1790, 2001.

Park, Y.S., and Y. Ito, "Micropattern-Immobilization of Heparin to Regulate Cell Growth With Fibroblast Growth Factor," *Cytotechnology* 33:117-122, 2000.

Persson, J., et al., "Polymer Recycling in Aqueous Two-Phase Extractions Using Thermoseparating Ethylene Oxide-Propylene Oxide Copolymers," *Journal of Chromatography B* 743(1-2):115-126, 2000.

Pettit, D.K., et al., "Influence of the Substrate Binding Characteristics of Fibronectin on Corneal Epithelial Cell Outgrowth," *J. Biomed. Mater. Res.* 26(10):1259-1275, Oct. 1992.

Priest, J.H., et al., *Lower Critical Solution Temperatures of Aqueous Co-polymers of N-Isopropylacrylamide and Other N-Substituted Acrylamides*, ACS Symposium Series 350, New York, New York, Apr. 13-18, 1986, pp. 255-264.

Sanford, M.S., et al., "Photoactivatable Cross-Linked Polyacrylamide for the Site-Selective Immobilization of Antigens and Antibodies," *Chem. Mater.* 10(6):1510-1520, 1998.

Schakenraad, J.M., et al., "The Influence of Substratum Surface Free Energy on Growth and Spreading of Human Fibroblasts in the Presence and Absence of Serum-Proteins," *J. Biomed. Mater. Res.* 20(6):773-784, Jul./Aug. 1986.

Shimizu, T., et al., "Two-Dimensional Manipulation of Cardiac Myocyte Sheets Utilizing Temperature-Responsive Culture Dishes Augments the Pulsatile Amplitude," *Tissue Engineering* 7(2):141-151, 2001.

Sigal, G.B., et al., "Effect of Surface Wettability on the Adsorption of Proteins and Detergents," *J. Am. Chem. Soc.* 120(14):3464-3473, 1998.

Sugiyama, K., et al., "Preparation and Application of Chiral Recognizable Thermosensitive Polymers and Hydrogels Consisting of N-Methacryloyl-s-Phenylalanine Methyl Ester," *J. Appl. Polym. Sci.* 82(1):228-236, 2001.

Takada, M., et al., "Interaction Parameters of Poly(Vinyl Methyl-Ether) in 2-Propanol Water Mixture as Determined by Small-Angle Neutron- Scattering," *Kobunshi Ronbunshu* 51(11):689-693, 1994. [Abstract].

Takahashi, M., et al., "Thermoreversible Gelation and Phase Separation in Aqueous Methyl Cellulose Solutions," *J. Polym. Sci. Part B: Polym. Phys.* 39(1):91-100, 2001.

Terada, T., et al., "Raman Spectroscopic Study on Water in Aqueous Solutions of Temperature-Responsive Polymers: Poly(N-Isopropylacrylamide) and Poly[N-(3-Ethoxypropyl)Acrylamide]," *Macromol. Chem. Phys.* 195(9):3261-3270, Sep. 1994.

Welin-Klintström, S., et al., "Surfactant and Protein Interactions on Wettability Gradient Surfaces," *J. Colloid Interface Sci.* 158:188-194, 1993.

Williams, D.F. (ed.), *Techniques of Biocompatibility Testing, vol. II*, CRC Press, Boca Raton, Florida, 1986, Chap. 9, "Techniques for Protein Adsorption Studies," pp. 184-212.

Wright, E.R., and V.P. Conticello, "Self-Assembly of Block Copolymers Derived From Elastin-Mimetic Polypeptide Sequences," *Advanced Drug Delivery Reviews* 54(8):1057-1073, 2002.

Wu, R.Z., et al., "Cell-Biological Applications of Transfected-Cell Microarrays," *Trends Cell Biol.* 12(10):485-488, Oct. 2002.

Xiong, X., et al., "Controlled Multibatch Self-Assembly of Microdevices," *J. Microelectromech. Sys.* 12(2):117-127, Apr. 2003.

Yamada, N., et al., *Makromolekulare Chemie, Rapid Communciations* 11(11):571-576, Nov. 1990.

Yamato, M., et al., "Novel Patterned Cell Coculture Utilizing Thermally Responsive Grafted Polymer Surfaces," *J. Biomed. Mater. Res.* 55(1):137-140, Apr. 2001.

Yamato, M., et al., "Release of Adsorbed Fibronectin From Temperature-Responsive Culture Surfaces Requires Cellular Activity," *Biomaterials* 21:981-986, 2000.

Yamato, M., et al., "Thermo-Responsive Culture Dishes Allow the Intact Harvest of Multilayered Keratinocyte Sheets Without Dispase by Reducing Temperature," *Tissue Engineering* 7(4):473-480, 2001.

Yousaf, M.N., et al., "Using Electroactive Substrates to Pattern the Attachment of Two Different Cell Populations," *Proc. Natl. Acad. Sci. USA* 98(11):5992-5996, May 22, 2001.

Zhong, Y.Z., and P. Wolf, "Effects of Hydrophobic Unit and Its Distribution on Solution Properties of Vinyl Pyrrolidone and Vinyl Acetate Copolymer," *J. Appl. Polym. Sci.* 74(2):345-352, 1999.

\* cited by examiner

APPARATUS AND METHODS FOR BINDING MOLECULES AND CELLS

CROSS-REFERENCE TO RELATED APPLICATION

This application claims the benefit of U.S. Provisional Application No. 60/399,793, filed Jul. 30, 2002.

GOVERNMENT RIGHTS

This invention was made with government support under Grant No. EEC-9529161 awarded by the National Science Foundation. The government has certain rights in the invention.

FIELD OF THE INVENTION

The present invention relates to devices for selectively and/or locally binding cells or proteins to a surface, such as silicon chips that include a temperature-responsive layer that binds cells or proteins when heated, and to methods for measuring the interaction between proteins and/or living cells in vitro.

BACKGROUND OF THE INVENTION

The ability to bind molecules (e.g., proteins) and living cells to a substrate is essential to the operation of many devices and procedures in biotechnology. For example, some techniques for high-throughput screening of candidate drugs use microchips (e.g., pieces of silicon, or glass, typically having dimensions of no more than a few centimeters) that include living cells attached to a microchip surface. The living cells are contacted with a candidate drug, and the response of the cell to the candidate drug is measured, thereby indicating whether the candidate drug may be effective to modulate a biochemical or physiological pathway implicated in a disease state. The small size of the microchips permits many candidate drugs to be simultaneously screened.

Again by way of example, immunoassays can be conducted using microchips that include antibody molecules attached to a microchip surface. The microchip is contacted with a fluid sample taken from an animal subject (e.g., a human being), and binding of the cognate antigen to the antibody molecules immobilized on the microchip is measured. For example, unlabelled antibody A, that specifically binds to one portion of an antigen called antigen A, is attached to a surface of a microchip, and the microchip is contacted with a fluid sample (e.g., human blood sample) that includes an unknown amount of antigen A, under conditions that permit binding of antigen A to immobilized antibody A. The fluid sample is then washed away, and the microchip is contacted with fluorescently-labelled antibody B that binds to a different portion of antigen A than does antibody A. The amount of fluorescent antibody B bound to antigen A is measured, thereby permitting calculation of the amount of antigen A bound to the microchip. The amount of antigen A present in the fluid sample can therefore be calculated.

Consequently, there is a continuing need for microchips, and other devices, that selectively bind living cells, proteins, or other molecules, to one, or more, specific locations on a surface of the device, and methods for making such devices. Preferably, the devices can bind most, or all, types of living cells and/or proteins.

SUMMARY OF THE INVENTION

In one aspect, the present invention provides devices for binding cells or molecules, wherein each device includes (a) a body defining a first surface and a second surface that is located opposite to the first surface; (b) a heater disposed upon the first surface; and (c) a temperature-responsive layer disposed upon the second surface, wherein the temperature-responsive layer comprises a temperature-responsive material that can exist in a first state that binds molecules or living cells, and can exist in a second state that binds substantially less molecules or living cells than the first state, and wherein the temperature-responsive material is reversibly convertible to the first state from the second state in response to an effective amount of thermal energy.

In another aspect, the present invention provides methods for binding molecules or living cells to a temperature-responsive material, wherein the methods each include the steps of contacting a temperature-responsive material with a population of molecules or a population of living cells, wherein: (a) the temperature-responsive material can exist in a first state that binds molecules or living cells, and can exist in a second state that binds substantially less molecules or living cells than the first state, and wherein the temperature-responsive material is reversibly convertible to the first state from the second state in response to an effective amount of thermal energy; and (b) the temperature-responsive material exists in the first state when the temperature-responsive material is contacted with the population of molecules or living cells, thereby effecting binding of the molecules or living cells to the temperature-responsive material.

In another aspect, the present invention provides methods for binding more than one type of molecule or more than one type of living cell to a temperature-responsive material, wherein the methods each include the steps of: (a) contacting a temperature-responsive material with a first type of molecules or a first type of living cells, wherein the temperature-responsive material is attached to a device body wherein the device body defines a first surface and a second surface that is located opposite the first surface, wherein a first population of heaters and a second population of heaters are disposed upon the first surface, and wherein the temperature-responsive material forms a temperature-responsive layer on the second surface; (b) activating the first population of heaters to heat a first population of temperature-responsive layer portions, located on the second surface opposite the first population of heaters, so that the first type of molecules or the first type of living cells binds to the first population of temperature-responsive layer portions, said activation occurring before or during the contacting of the temperature-responsive material with the first type of molecules or the first type of living cells; (c) removing any of the first type of molecules or the first type of living cells that are not bound to the first population of temperature-responsive layer portions; (d) contacting the temperature-responsive material with a second type of molecules or a second type of living cells; (e) activating the second population of heaters to heat a second population of temperature-responsive layer portions, located on the second surface opposite the second population of heaters, so that the second type of molecules or the second type of living cells binds to the second population of temperature-responsive layer portions, said activation occurring before or during the contacting of the temperature-responsive material with the second type of molecules or the second type of living cells; and (f) removing any of the second type of molecules or the second type of living cells that are not bound to the second population of temperature-responsive layer portions.

In another aspect, the present invention provides methods for measuring a response of a population of living cells to an agent, wherein the methods of this aspect of the invention each include the steps of contacting a population of living cells with an agent and measuring a response of the living cells to the agent. The living cells are attached to a temperature-responsive material that can exist in a first state that binds living cells, and can exist in a second state that binds substantially less living cells than the first state, wherein the temperature-responsive material is reversibly convertible to the first state from the second state in response to an effective amount of thermal energy. The temperature-responsive material exists in the first state while the living cells are contacted with the agent.

In another aspect, the present invention provides methods for observing the binding of members of a binding pair, wherein the methods each include the steps of contacting a first member of a binding pair with a second member of a binding pair and observing the binding of the first member of the binding pair with the second member of the binding pair. The first member of the binding pair is attached to a temperature-responsive material that can exist in a first state that binds the first member of the binding pair, and can exist in a second state that binds substantially less first member of the binding pair than the first state, wherein the temperature-responsive material is reversibly convertible to the first state from the second state in response to an effective amount of thermal energy. The temperature-responsive material exists in the first state while the first member of the binding pair is contacted with the second member of the binding pair.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

In one aspect, the present invention provides devices for binding cells or molecules, wherein each device includes (a) a body defining a first surface and a second surface that is located opposite to the first surface; (b) a heater disposed upon the first surface; and (c) a temperature-responsive layer disposed upon the second surface, wherein the temperature-responsive layer comprises a temperature-responsive material that can exist in a first state that binds molecules or living cells, and can exist in a second state that binds substantially less molecules or living cells than the first state, and wherein the temperature-responsive material is reversibly convertible to the first state from the second state in response to an effective amount of thermal energy.

The phrase "a second state that binds substantially less molecules or living cells than the first state" means that the second state of a temperature responsive material binds less than 15% of the molecules, or living cells, bound by the first state of the same temperature responsive material, under the same binding conditions and given the same amount of time for binding to occur. In some embodiments, the second state of a temperature responsive material binds less than 10% of the molecules or living cells bound by the first state of the same temperature responsive material, under the same binding conditions and given the same amount of time for binding to occur. In some embodiments, the second state of a temperature responsive material binds less than 5% of the molecules or living cells bound by the first state of the same temperature responsive material, under the same binding conditions and given the same amount of time for binding to occur.

Figure 1:
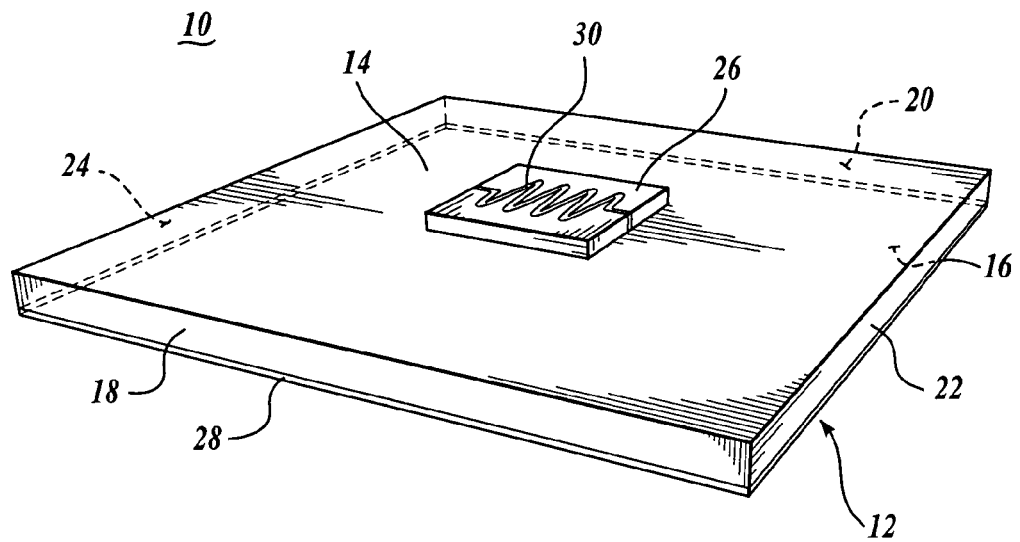
FIG. 1 shows a perspective view of a representative device of the present invention viewed in the direction of a first surface.
Figure 2:
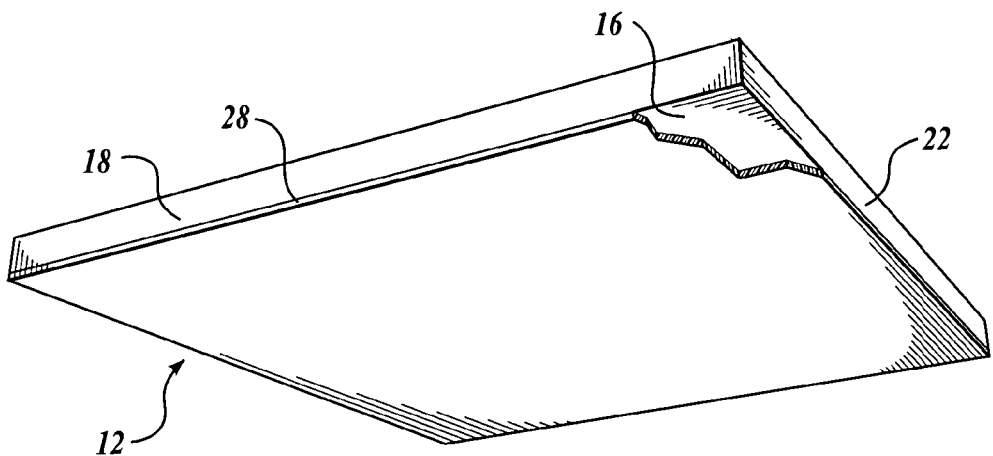
FIG. 2 shows a perspective view of the device shown in FIG. 1 viewed in the direction of a second surface located opposite the first surface, and showing a partially cut-away temperature-responsive layer.
Figure 3:
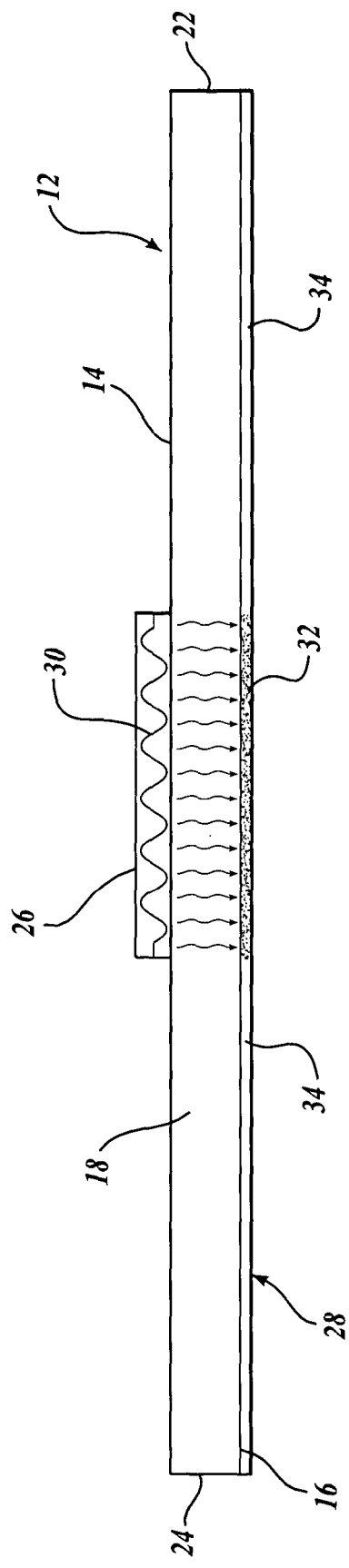
FIG. 3 shows a side view of the device shown in FIGS. 1 and 2.

FIG. 1 shows a perspective view of a representative device 10 of the present invention. Device 10 includes a body 12 defining a first surface 14, a second surface 16 located opposite to first surface 14, a first face 18, a second face 20, a first end 22 and a second end 24. A heater 26 is disposed on first surface 14, and a temperature-responsive layer 28 is disposed on second surface 16. FIG. 2 shows a perspective view of second surface 16 of device 10 with temperature-responsive layer 28 partially cut away to more clearly show second surface 16. Heater 26 includes heating element 30. FIG. 3 shows a side view (looking at first face 18) of representative device 10 shown in FIGS. 1 and 2.

In operation, application of an electrical current, or electrical potential, to heating element 30 generates heat that is transferred to a portion 32 of temperature-responsive layer 28 that is located opposite heater 26 (in FIG. 3 the localized transfer of heat is represented by arrows extending between heater 26 and temperature-responsive layer portion 32). All of temperature-responsive layer 28 that is not heated by heater 26 is unheated portion 34 of temperature-responsive layer 28.

Temperature-responsive layer 28 includes a temperature-responsive material that can exist in two states: a first state that binds molecules or living cells, and a second state that binds substantially less molecules or living cells than the first state (e.g., binds no, or almost no, molecules or living cells). The temperature-responsive material is reversibly convertible to the first state from the second state in response to an effective amount of thermal energy. Thus, heating the temperature-responsive material to an appropriate temperature causes it to exist in the first state and to more effectively bind molecules or living cells. Typically, binding of molecules or living cells occurs in an aqueous environment. Thus, for example, to bind molecules (e.g., proteins, such as antibodies), or living cells, to portion 32 of temperature-responsive layer 28, portion 32 is heated so that temperature-responsive material exists in the first state, and portion 32 is contacted with an aqueous solution of the molecules, or a preparation of living cells present in an aqueous medium (e.g., cell culture medium). The molecules or cells preferentially bind to heated portion 32, and bind substantially less efficiently to unheated portion 34. Thereafter, device 10 may be washed with an aqueous solution to remove unbound cells or molecules.

Figure 4:
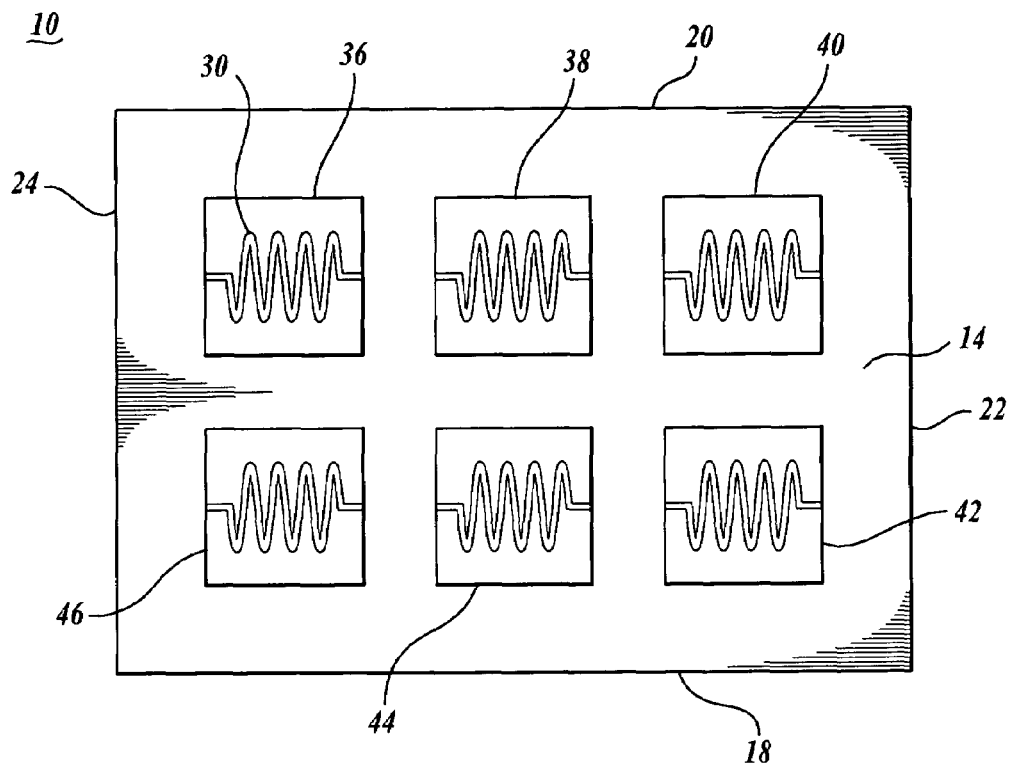
FIG. 4 shows a plan view of another representative device of the present invention that includes six heaters.

Some embodiments of device 10 of the invention include multiple heaters 26 which may be ordered in an array on first surface 14. For example, FIG. 4 shows a plan view of a representative device 10 (looking at first surface 14) that includes six heaters 26, identified as first heater 36, second heater 38, third heater 40, fourth heater 42, fifth heater 44, and sixth heater 46, arrayed on first surface 14. In embodiments of device 10 that include a multiplicity of heaters 26, some, or all, of heaters 26 may be controlled independently of other heaters 26 so that some heaters 26 are heating while other heaters 26 are not. Thus, these embodiments of device 10 permit some (optionally multiple) portions of temperature-responsive layer 28 to be heated (and so exist in a binding state), while other portions of temperature-responsive layer 28 are not heated (and so exist in a non-binding state). These embodiments of device 10 are useful for simultaneously binding more than one type of molecule and/or living cell to temperature-responsive layer 28.

Figure 5:
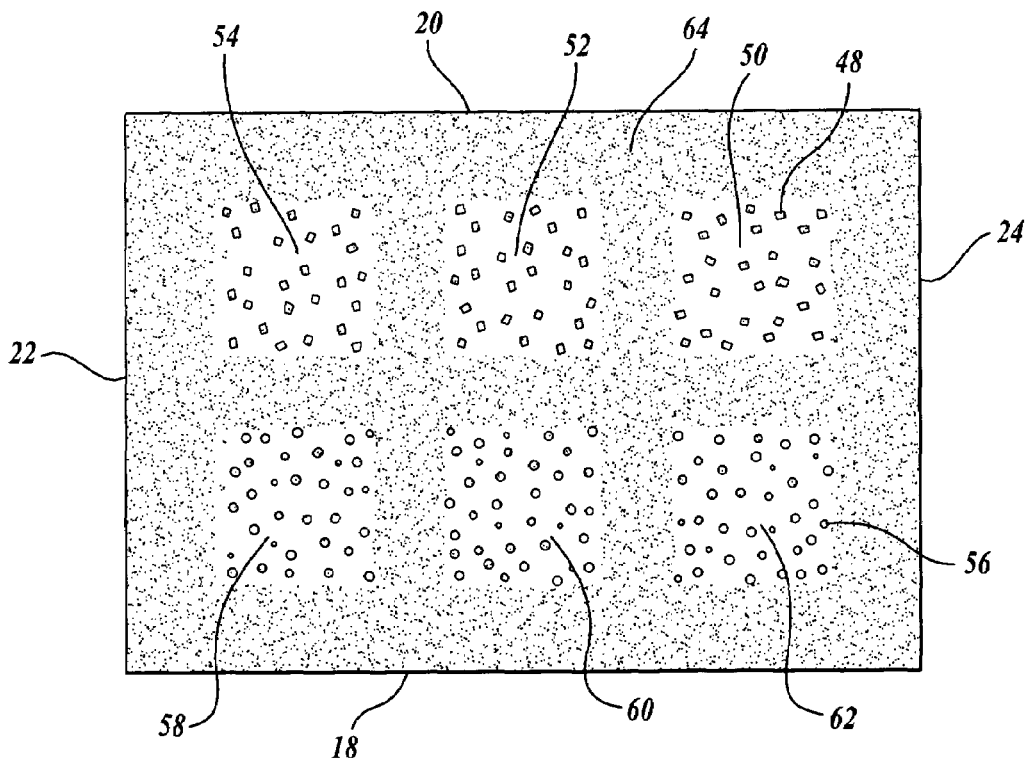
FIG. 5 shows a plan view of the device shown in FIG. 4 (viewed in the direction of the surface opposite the surface shown in FIG. 4).

Thus, for example, FIG. 5 shows a plan view (looking at second surface 16) of the embodiment of device 10 shown in FIG. 4, in which a first cell type 48 (represented by squares in FIG. 5) is attached to a first temperature-responsive layer portion 50 located on second surface 16 opposite first heater 36, and to a second temperature-responsive layer portion 52 located on second surface 16 opposite second heater 38, and to a third temperature-responsive layer portion 54 located on second surface 16 opposite third heater 40. A second cell type 56 (represented by circles in FIG. 5) is attached to a fourth temperature-responsive layer portion 58 located on second surface 16 opposite fourth heater 42, and to a fifth temperature-responsive layer portion 60 located on second surface 16 opposite fifth heater 44, and to a sixth temperature-responsive layer portion 62 located on second surface 16 opposite sixth heater 46. The embodiment of device 10 shown in FIGS. 4 and 5 therefore includes six, separate, temperature-responsive layer portions 50, 52, 54, 58, 60 and 62, that each have living cells attached to them, while no other portion of temperature-responsive layer 28 has living cells attached to it (or living cells are attached in an amount, and at a density, substantially lower than is found on temperature-responsive layer portions 50, 52, 54, 58, 60 and 62). Thus, temperature-responsive layer portion 64 (represented by stippling in FIG. 5) encompasses all of temperature-responsive layer 28 except for temperature-responsive layer portions 50, 52, 54, 58, 60 and 62, and either has no living cells attached to it, or living cells are attached to temperature-responsive layer portion 64 in an amount, and at a density, substantially lower than is found on temperature-responsive layer portions 50, 52, 54, 58, 60 and 62.

The embodiment of device 10 shown in FIG. 5 can be made, for example, by activating first heater 36, second heater 38, and third heater 40, so that first temperature-responsive layer portion 50, second temperature-responsive layer portion 52, and third temperature-responsive layer portion 54 are heated and exist in a first (binding) state, while the remainder of temperature-responsive layer 28 remains in a second (non-binding) state. Temperature-responsive layer 28 is contacted with an aqueous medium type 48 does not bind to any other portion of temperature-responsive layer 28 except for heated portions 50, 52 and 54; or, if cell type 48 does bind to another portion of temperature-responsive layer 28, in addition to heated portions 50, 52 and 54, binding is substantially less efficient than to heated portions 50, 52 and 54.

After first cell type 48 has bound to heated portions 50, 52 and 54 of temperature-responsive layer 28, aqueous medium that includes first cell type 48 is removed, and fourth heater 42, fifth heater 44, and sixth heater 46 are activated, so that fourth temperature-responsive layer portion 58, fifth temperature-responsive layer portion 60, and sixth temperature-responsive layer portion 62 are heated and exist in a first (binding) state. Portions 50, 52 and 54 of temperature-responsive layer 28 also continue to be heated to prevent first cell type 48 from detaching therefrom. Temperature-responsive layer 28 is then contacted with an aqueous medium that includes second cell type 56 which preferentially bind to heated portions 58, 60 and 62. Heated portions 50, 52 and 54 of temperature-responsive layer 28 are saturated with first cell type 48, and so bind little, if any, second cell type 56. All unheated portions of temperature-responsive layer 28 exist in a second (non-binding) state, and so bind few, if any, second cell type 56. Temperature-responsive layer 28 is then washed to remove unbound second cell type 56.

Thus, in some embodiments, device 10 includes molecules (such as proteins) or one or more living cell(s) bound to one, or more, portions of temperature-responsive layer 28, but not to the entire surface of temperature-responsive layer 28. Some embodiments of device 10 include several portions of temperature-responsive layer 28 that each have a single living cell bound thereto. The same type of living cell may be bound to each of the different portions of temperature-responsive layer 28, or a different type of living cell may be bound to some, or all, of the different portions of temperature-responsive layer 28.

Examples of types of cells that can be attached to one or more portions of temperature responsive layer 28 include granulocytes, chondrocytes, endothelial cells, neural cells, hepatocytes, fibroblasts, epithelial cells, monocytes, polymorphonuclear leukocytes, microglia, cardiac myocytes, keratinocyte, primary bovine aortic smooth muscle cells and human embryonic kidney cells.

Examples of molecules that can be attached to one or more portions of receptors. In the context of the present patent application, the term "antibody" includes, but is not limited to, polyclonal and monoclonal antibody preparations, CDR-grafted antibody preparations, as well as preparations including hybrid antibodies, altered antibodies, F(AB)′$_2$ fragments, F(AB) molecules, Fv fragments, single domain antibodies, chimeric antibodies and functional fragments thereof which exhibit immunological binding properties of the parent antibody molecule.

The following description of the elements of devices 10 of the present invention is made with reference to the embodiment of device 10 shown in FIGS. 1, 2 and 3, but applies to all embodiments of device 10, such as the embodiment shown in FIGS. 4 and 5, that include the described elements. Device body 12 can be made from any electrical or thermal insulator material, such as a plastic or mineral that possesses electrical and thermal insulating properties that prevents most, preferably all, of the heat generated by heater 26 from heating any portion of temperature-responsive layer 28, except portion 32 on second surface 16 opposite heater 26. Representative examples of materials useful for making body 12 include glass, silicon, mica, quartz, sapphire, silicon nitride membrane, silicon dioxide membrane, polytetrafluoroethylene (sold by DuPont under the tradename Teflon®), and poly (ethyleneterephthalate) (sold by DuPont under the tradename Mylar®). Device body 12 can have any desired size and shape. For example, device body 12 can be square, rectangular or circular.

The length, width, and height of a rectangular or square device body 12 may each be, for example, from 1 to 10 millimeters, or, for example, from 1 to 10 centimeters. The maximum width of device body 12 (whether device body 12 is a regular or irregular geometric shape) may be, for example, from 1 to 10 millimeters, or, for example, from 1 to 10 centimeters. The height may be, for example, from 1 to 100 micrometers. Body 12 may have a thickness, for example, in the range of from 0.0001 mm to 2 mm.

Heaters 26 useful in the practice of the invention produce sufficient heat to cause temperature-responsive layer 28 to change from a first (binding) state to a second (non-binding) state. In embodiments of device 10 that include multiple heaters 26, heaters 26 are disposed on first surface 14 so that there is sufficient distance between adjacent heaters 26 to prevent heat from one heater 26 from spreading to an adjacent heater 26 under normal operating conditions. Embodiments of device 10 that include multiple heaters 26 may include, for example, 1, 2, 3, 4, 5, 6, 7, 8, 9, or 10 heaters 26, or may include, for example, between 10 and 50 heaters 26, or may include, for example, between 10 and 100 heaters 26. Multiple heaters 26 may be arranged in any pattern, including regular geometric shapes (e.g., rectangular or square arrays), or any irregular pattern.

Heater 26 includes heating element 30, which may be a narrow, thin, film made from metal (see, e.g., K. Henning, et al., In Proc. International Solid State Sensors and Actuators Conference, pp. 825-828 (1997)), or polysilicon (see, e.g., S. W. Janson, Batch-Fabricated Resistojets: Initial Results, In International Electric Propulsion Conference. Cleveland, Ohio, USA IEPC-97-070, (1997)) as a resistor to generate heat over a defined surface area. An electrical current or voltage is applied to heating element 30 to generate heat in accordance with Joule's law.

Heater 26 may be directly deposited onto body 12 which can be, for example, silicon wafer, a glass slide, mica, quartz or plastic. In some cases heater 26 is suspended on a thin membrane (e.g., silicon nitride) in order to minimize conductive heat losses (see, e.g., S. W. Janson, Batch-Fabricated Resistojets: Initial Results, In International Electric Propulsion Conference. Cleveland, Ohio, USA IEPC-97-070, (1997)). Heater 26 may be driven by an electric current via a current source, or electric voltage via a voltage source (see, e.g., Chen, J. K. and Wise, K. D., "A Silicon Probe with Integrated Microheaters for Thermal Marking and Monitoring of Neural Tissue," *IEEE Trans. Biomed. Eng.* 44:770-774 (1997)). Temperature sensors may be included on body 12 to monitor the temperature, and heater 26 may be used as a temperature sensor (see, e.g., Baroncini, M., et al., Characterization of an embedded micro-heater for gas sensors applications VLSI Technology, Systems, and Applications, 2001. Proceedings of Technical Papers. 2001 International Symposium on 18-20 Apr. 2001 Page(s): 164-167; P. Ruther, et al., Dependence of the Temperature Distribution in Micro Hotplates on Heater Geometry and Heating Mode, Proc. Transducers '03, p. 73-76, (2003)).

Heater 26 may be made, for example, by metal deposition and patterning. Metal deposition methods include thermal evaporation deposition, sputtering, thermal spray coating, chemical vapor deposition (CVD), electroplating, or other electroless metal plating. Patterning methods include photolithography, soft lithography, and electron beam lithography. Etching methods include wet etching, plasma etching, ion milling, reactive ion etching, laser etching and liftoff. Other electrically conductive materials, such as poly-silicon, can also be used to make heater 26. Representative methods for making heaters 26 are described, for example, in Gregory T. A. Kovacs, *Micromachined Transducers Soucebook*, WCB/McGraw-Hill, 1998; and in Stephen A. Campbell, *The Science and Engineering of Microelectronic Fabrication*, Oxford University Press, 1996. With the development of nanotechnology, it is also possible to grow nanowires for use as heating element 30 which greatly reduces the size of heater 26 [see, e.g., S. Matsui, Three-Dimensional Nanostructure Fabrication by Focused-Ion-Beam Chemical Vapor Deposition, Proc. Transducers '03, p. 179-181 (2003)].

Micro inductor arrays can also be used as heater 26 in the practice of the present invention (see, e.g., Jae Y. Park and Mark G. Allen, "High Current Integrated Microinductors and Microtransformers using Low Temperature Fabrication Processes", 29th International Symposium on Microelectronics, Minneapolis, Minn., October, 1996).

Heater 26 can also use chemical reactions to generate heat. Microwell arrays integrated with micro fluid channels can deliver chemicals to a specific site. Micro fluid channels can be fabricated on various substrates, such as silicon, glass, mica, or plastic. Chemical transportation can be achieved, for example, by built-in or external pumps. Fluid channels can dispose of waste and import new chemicals.

Temperature-responsive layer 28 is made from any temperature-responsive material, or mixture or blend of temperature-responsive materials, that can exist in a first state that binds molecules or living cells, and that can exist in a second state that binds substantially less molecules or living cells than the first state, and wherein temperature-responsive layer 28 is reversibly convertible to the first state from the second state in response to an effective amount of thermal energy. Temperature-responsive layer 28 may be, for example, only a single layer of molecules of temperature responsive material. Conversion of temperature-responsive layer 28 to the first (binding) state from the second (non-binding) state occurs at a temperature above the lower critical solution temperature (LCST) of the temperature-responsive material used to make temperature-responsive layer 28. Conversion of temperature-responsive layer 28 to the second (non-binding) state from the first (binding) state occurs at a temperature below the lower critical solution temperature of the temperature-responsive material used to make temperature-responsive layer 28. Thus, heating temperature-responsive layer 28 above the LCST of the temperature-responsive material from which temperature-responsive layer 28 is made causes temperature-responsive layer 28 to exist in a first (binding) state that preferentially binds molecules and/or living cells. While not wishing to be bound by theory, the enhanced ability of the temperature-responsive materials of the present invention to bind cells and/or molecules above their LCST may be due to a change in conformation of the molecules in the temperature-responsive materials that exposes more chemical groups (e.g., NH and C=O) that can form hydrogen bonds with molecules and/or cells in an aqueous environment.

For example, poly (N-isopropylacrylamide) (abbreviated as pNIPAM) is useful for making temperature-responsive layer 28 and has an LCST of 31° C. Above 31° C. pNIPAM exists in a binding state that binds molecules and living cells; whereas below 31° C. pNIPAM exists in a non-binding state that binds molecules and living cells substantially less efficiently than the binding state.

Temperature-responsive layer 28 is typically, although not necessarily, made from a material that possesses a critical solution temperature (LCST) below 37° C. in an aqueous environment. The following materials are representative examples of materials useful for making temperature-responsive layer 28 (the temperature in parentheses after the name of the material is the LCST for the material, and the citation(s) that follow the name of each material provides a description of that material, or class of materials): homopolymers and copolymers of poly-N-alkyl-substituted acrylamides such as poly(N,N-dimethylacrylamide) (33° C.) (Idziak, I., et al., *Macromolecules* 32(4):1260-1263, 1999), poly(ethylacrylamide)(15° C.)(Park, S. Y., et al., *European Polymer Journal* 37(9):1785-1790, 2001), poly(N-ethylmethacrylamide) (Bohdanecky, M., et al., *Collection of Czechoslovak Chemical Communications,* 58(10):2370-2382, 1993), poly[N-(3-ethoxypropyl)acrylamide] (24.5° C.) (Terada, T., et al., *Macromolecular Chemistry and Physics* 195(9):3261-3270, 1994), poly[N-(2-hydroxypropyl)methacrylamide] (16-20° C.) (Sugiyama, K., et al., *Journal of Applied Polymer Science*

82(1):228-236, 2001), poly(N-vinylisobutyramide) (39° C.) (Kunugi, S., et al., *Polymer Journal* 34(5):383-388, 2002) and poly(N-vinylacetamide) (25° C.) (Hong, J. S., et al., *Colloid and Polymer Science* 274(11):1013-1019, 1996).

Other materials useful for making temperature-responsive layer 28 include copolymers and derivatives of methylene oxide (Benkhira, A., et al., *Polymer* 41(20):7415-7425, 2000), polyethylene oxide and propylene oxide (30-50° C.) (Persson, J., A. Kaul, and F. Tjerneld, *Journal of Chromatography B* 743(1-2):115-126, 2000), such as copolymers of methoxy poly(ethylene glycol) and poly(propylene fumarate) and vinyl ethers of ethylene glycol (20-90° C.) (Kudaibergenov, S. E., et al., *Macromolecular Rapid Communications* 16(11):855-860, 1995). Cellulose and derivatives, such as hydroxypropylcellulose (Hirsch, S. G. and R. J. Spontak, Polymer 43(1):123-129, 2002), ethyl hydroxyethyl cellulose (Badiger, M. V., A. Lutz, and B. A. Wolf, *Polymer* 41(4):1377-1384, 2000), and methyl cellulose (29° C.) (Takahashi, M., M. Shimazaki, and J. Yamamoto, *Journal of Polymer Science Part B-Polymer Physics* 39(1):91-100, 2001) can also be used to make temperature-responsive layer. Polyethers such as poly(vinyl methyl ether) (33° C.) (Takada, M., et al., *Kobunshi Ronbunshu* 51(11):689-693, 1994), butyl vinyl ether (20-90° C.) (Kudaibergenov, S. E., et al., *Macromolecular Rapid Communications* 16(11):855-860, 1995) and polyglycidol (4-100° C.) (Dworak, A., et al., *Polymer Bulletin* 50(1-2):47-54, 2003) can also be used to make temperature-responsive layer 28.

Other materials useful for making temperature-responsive layer 28 include polyesters, such as acryloyl-L-proline methyl ester (10-18° C.) (Hiroki, A., et al., *Journal of Polymer Science Part A-Polymer Chemistry* 36(10):1495-1500, 1998), poly(N-acryloylamino amide)(3-35° C.) derivatives (Dobashi, A., K. Kurata, and M. Senoo, *Analytical Sciences* 16(8):829-835, 2000), vinyl pyrrolidone and vinyl acetate copolymers (Zhong, Y. Z. and P. Wolf, *Journal of Applied Polymer Science* 74(2):345-352, 1999), copolymer of N-acryloyl-N'-alkyl piperazine and methyl methacrylate (22-42° C.) (Gan, L. H., et al., Polymer 42(1):65-69, 2001), homopolymer and copolymer of polyacrylate such as poly (methyl 2-propionamidoacrylate) (Okamura, H., et al., Polymer 43(13):3825-3828, 2002), poly(ethylene oxide)-modified poly(acrylic acid)(20-60° C.) (Dorn, I., et al., *Langmuir* 14:4386-4842, 1998) and poly(acrylic acid) (PAAc) and poly (acrylamide-co-butyl methacrylate) (10-30° C.) (Katono, H., et al., *Journal of Controlled Release* 16(1-2):215-227, 1991). Additionally, by way of example, poly(organophosphazenes) (37-75° C.) (Lee, B. H., et al., *Macromolecules* 35(10):3876-3879, 2002), Poly(2-ethyl-2-oxazoline) (PEtOx) (Christova, D., et al., *Polymer* 44(8):2255-2261, 2003), Gelatin (Aso, Y., et al., *Radiation Physics and Chemistry* 55(2):179-183, 1999), poly(N-vinylcaprolactam) (33° C.) (Loos, W., et al., *Macromolecular Chemistry and Physics* 204(1)1:98-103, 2003), elastin and elastin mimetic polypeptide (33-35° C.) (Wright, E. R. and V. P. Conticello, *Advanced Drug Delivery Reviews* 54(8):1057-1073, 2002), 2,4,6-trimethylpyridine (5.5° C.) (Marczak, W. and A. Banas, Fluid Phase Equilibria 186(1-2):151-164, 2001) and poly(N-vinylpyrrolidone) (32.5° C.) (Maeda, Y., T. Nakamura, and I. Ikeda, *Macromolecules* 35(1):217-222, 2002) can also be used to make temperature-responsive layer 28.

In another aspect, the present invention provides methods for binding molecules or living cells (or a single living cell) to a temperature-responsive material, wherein the methods each include the step of contacting a temperature-responsive material with a population of molecules or a population of living cells (or a single living cell), wherein: (a) the temperature-responsive material can exist in a first state that binds molecules or living cells, and can exist in a second state that binds substantially less molecules or living cells than the first state, and wherein the temperature-responsive material is reversibly convertible to the first state from the second state in response to an effective amount of thermal energy; and (b) the temperature-responsive material exists in the first state when the temperature-responsive material is contacted with the population of molecules or living cells (or the single living cell), thereby effecting binding of the molecules or living cell(s) to the temperature-responsive material.

In some embodiments of the methods of this aspect of the present invention, the temperature-responsive material forms a layer on a surface of a device body. In some embodiments, the device body defines a first surface and a second surface that is located opposite the first surface, wherein a heater is disposed upon the first surface, the temperature-responsive material forms a layer on the second surface, and the heater heats the temperature-responsive material so that the temperature-responsive material exists in the first state and binds the molecules or living cells.

In other embodiments of the methods of this aspect of the present invention, more than one type of molecule or more than one type of living cell is bound to a temperature-responsive material. These method include the steps of: (a) contacting a temperature-responsive material with a first type of molecules or a first type of living cell(s), wherein the temperature-responsive material is attached to a device body wherein the device body defines a first surface and a second surface that is located opposite the first surface, wherein a first population of heaters and a second population of heaters are disposed upon the first surface, and wherein the temperature-responsive material forms a temperature-responsive layer on the second surface; (b) activating the first population of heaters to heat a first population of temperature-responsive layer portions, located on the second surface opposite the first population of heaters, so that the first type of molecules, or the first type of living cell(s), binds to the first population of temperature-responsive layer portions, said activation occurring before or during the contacting of the temperature-responsive material with the first type of molecules or the first type of living cell(s); (c) removing any of the first type of molecules, or the first type of living cell(s), that are not bound to the first population of temperature-responsive layer portions; (d) contacting the temperature-responsive material with a second type of molecules or a second type of living cell(s); (e) activating the second population of heaters to heat a second population of temperature-responsive layer portions, located on the second surface opposite the second population of heaters, so that the second type of molecules, or the second type of living cell(s), binds to the second population of temperature-responsive layer portions, said activation occurring before or during the contacting of the temperature-responsive material with the second type of molecules or the second type of living cell(s); and (f) removing any of the second type of molecules, or the second type of living cell(s), that are not bound to the second population of temperature-responsive layer portions. In embodiments of these methods, wherein a first type of living cell(s) is bound to the first population of temperature-responsive layer portions, and a second type of living cell(s) is bound to the second population of temperature-responsive layer portions, the first population of heaters typically remains activated while the second population of heaters are activated, so that the first type of living cell(s) do not detach from the first population of temperature-responsive layer portions while the second type of living cell(s) is/are being bound to the second population of temperature-responsive layer portions.

Temperature-responsive materials useful in construction of device 10 of the present invention are also useful in the practice of the methods for binding molecules or living cells to a temperature-responsive material.

Molecules that can be bound to a temperature-responsive material include proteins, such as antibodies. Any type of living cell can be bound to a temperature-responsive material, including the representative cell types disclosed, supra, in connection with device 10 of the invention.

Devices 10 of the present invention are useful in the practice of the methods of the present invention for binding molecules or living cells to a temperature-responsive material (e.g., with reference to device 10 shown in FIGS. 1, 2 and 3, heater 26 heats portion 32 of temperature-responsive layer 28 so that portion 32 exists in a first (binding) state and binds molecules or living cells). It is not necessary, however, to use devices 10 to practice all embodiments of the methods of the present invention for binding molecules or living cells to a temperature-responsive material. For example, a layer of temperature-responsive material may be formed on a substrate (e.g., a silicon chip), and all, or a portion, of the layer of temperature-responsive material is heated by any useful means, so that the heated material exists in a first (binding) state and binds molecules or living cells. For example, all, or a portion, of the layer of temperature-responsive material can be heated by a direct, or indirect, contact with a heater that includes a heating element that produces heat in response to an electrical current, or potential difference, in accordance with Joule's law, or, for example, heat may be applied by an optical device such as a laser beam, or by direct, or indirect, contact with a hot chemical.

Devices 10 and methods for binding molecules or living cells to a temperature-responsive material can be used, for example, to study the interactions between living cells, and/or between living cells and their environment. Thus, for example, devices 10 of the present invention can be used to study the interaction of first cell type 48 with second cell type 56 in an aqueous environment (e.g., study the physiological response of first cell type 48 to soluble biological molecules released by second cell type 56). For example, first cell type 48 may be attached to first portion 50 of temperature-responsive layer 28 of device 10 shown in FIG. 5, and second cell type 56 may be attached to second portion 52 of temperature-responsive layer 28 of device 10 shown in FIG. 5. The distance between first portion 50 and second portion 52 is determined by the distance between first heater 36 and second heater 38. First cell type 48 and second cell type 56 are each completely, or partially, immersed in an aqueous medium. One or more physiological responses of first cell type 48 to soluble biological molecules released by second cell type 56 can be studied (e.g., by measuring the uptake or release of measurably labeled chemicals by first cell type 48).

Again by way of example, different cell types can be attached to different portions of temperature-responsive layer 28, and each cell type can be exposed to the same environmental stimulus, and the response of each cell type to the stimulus can be determined and compared.

Again by way of example, devices 10 of the present invention can be used to culture different cell types in physical proximity to each other in vitro. For example, cell interaction between liver cells and fibroblasts has been reported to modulate liver cell growth, migration, and/or differentiation in both the developing and adult liver in vivo. Cocultivation of these two types of cells, in vitro, on devices 10 of the present invention can be used to preserve and modulate hepatocyte phenotype and function for growing bioactive liver tissue in vitro.

Again by way of example, cell-based drug screening can be performed by attaching one, or more, types of cells to temperature-responsive layer 28 of device 10 of the present invention. The attached cells are then contacted with a candidate drug, and the response to the candidate drug is determined and compared to control cells that were not contacted with the candidate drug (e.g., the control cells may be attached to a different, but otherwise identical, device 10 as the cells that are contacted with the drug). Candidate drugs that elicit a desired response in the cells can be further evaluated for their suitability as drugs for administration to humans or other mammals (see, generally., Bailey, S. N., R. Z. Wu, and D. M. Sabatini, "Applications of transfected cell microarrays in high-throughput drug discovery," *Drug Discovery Today* 7(18):S113-S118, 2002).

Again by way of example, antibody molecules can be attached to temperature-responsive layer 28. For example, to identify an antigen that binds to a specific antibody (or vice versa) different antibodies can be attached to different portions of temperature-responsive layer 28 on device 10 (e.g., different antibodies can be attached to portions 50, 52, 54, 58, 60 and 62 of the embodiment of device 10 shown in FIG. 5). Device 10 is then contacted with one or more labeled antigens (e.g., fluorescently labeled antigens). Binding of an antigen to a specific antibody can be visualized, for example, with fluorescence microscopy, thereby identifying the binding antigen.

Similarly, one or more candidate antigens can be attached to different portions of temperature-responsive layer 28 (e.g., different antigens can be attached to portions 50, 52, 54, 58, 60 and 62 of the embodiment of device 10 shown in FIG. 5), and then temperature-responsive layer 28 is contacted with one or more labeled antibodies (different antibodies bear a different label if a mixture of antibodies is used). Binding of an antibody to a specific antigen can be visualized, for example, with fluorescence or light microscopy, thereby identifying the antibody that binds to a particular antigen.

Again by way of example, devices 10 can be used to conduct multiple immunoassays simultaneously. Thus, for example, with reference to the embodiment of device 10 shown in FIG. 5, six different, unlabelled, antibodies, each having a known specificity for a specific protein or metabolite occurring in human blood, are attached to portions 50, 52, 54, 58, 60 and 62 of temperature-responsive layer 28. The first antibody is attached to first portion 50, the second antibody is attached to second portion 52, the third antibody is attached to third portion 54, the fourth antibody is attached to fourth portion 58, the fifth antibody is attached to fifth portion 60, and the sixth antibody is attached to sixth portion 62. Temperature-responsive layer 28 is contacted with a sample of human blood under conditions that permit the binding of antigens to the antibodies. The blood sample is washed away, and temperature-responsive layer 28 is contacted with a solution containing fluorescently-labeled first, second, third, fourth, fifth and sixth antibodies (that recognize a different portion of the antigen recognized by unlabelled first, second, third, fourth, fifth and sixth antibodies, respectively), wherein the six different antibodies are each labeled with a different fluorescent compound, and the fluorescence produced by each of the six different fluorescent compounds can be distinguished from the fluorescence produced by each of the other five fluorescent compounds. The fluorescence produced by each of the six labeled antibodies is measured and the resulting values used to calculate the amount of each of the six antigens present in the blood sample.

Again by way of example, the present invention can be used to identify proteases and/or kinases that have substrate specificities that make them attractive candidates as drug targets. For example, one or more candidate proteases and/or kinases are attached to temperature-responsive layer 28 of device 10. Temperature-responsive layer 28 is then contacted with a fluorogenic or colorimetric substrate. A fluorescent or color signal is produced when the substrate is acted upon (e.g., cleaved or otherwise chemically converted) by a protease and/or kinase, thereby identifying a protease and/or kinase which utilizes the labeled molecule as a substrate.

Again by way of example, the present invention can be used to characterize the effect(s) on living cells caused by specific proteins (e.g., proteins that are suspected of causing a disease state). Thus, for example, protein molecules are attached to temperature-responsive layer 28 of device 10, and living cells are thereafter cultured on temperature-responsive layer 28. The growth, development, physiology and/or biochemistry of the cultured cells is then analyzed to identify any effect thereon caused by the protein molecules.

Thus, in another aspect, the present invention provides methods for measuring a response of a population of living cells (or a single living cell) to an agent, wherein each of the methods includes the steps of contacting a population of living cells (or a single living cell) with an agent and measuring a response of the living cell(s) to the agent. The living cell(s) is/are attached to a temperature-responsive material that can exist in a first state that binds living cells, and can exist in a second state that binds substantially less living cells than the first state, wherein the temperature-responsive material is reversibly convertible to the first state from the second state in response to an effective amount of thermal energy. The temperature-responsive material exists in the first state while the living cell(s) is/are contacted with the agent.

The agent can be any physical or energetic agent that elicits a response from living cells. For example, the agent can be a chemical molecule (e.g., proteins, nucleic acids), or an energetic stimulus, such as ionizing radiation. The living cells can be any living cells (e.g., mammalian cells, such as the representative mammalian cells disclosed supra). Examples of useful temperature-responsive materials are provided herein in connection with devices 10 of the invention. Typically, the living cells are completely, or partially, covered with an aqueous medium (e.g., cell culture medium) which provides moisture and nourishment to the cells. A soluble agent (e.g., some candidate drug molecules) can be dissolved in the aqueous medium, thereby contacting the living cells.

A response of the living cell(s) to the agent can be measured by any useful means, and the choice of measuring methods and devices depends, to a large extent, on the nature of the response. Representative examples of cell responses that can be measured using the methods of this aspect of the present invention include change in cell morphology, adhesiveness to a substrate, viability, migration, growth, multiplication, ability to uptake or secrete molecules (as a measure of the function of cell membrane channels and transport proteins), protein expression level in the cells, expression of DNA molecules introduced into the cells, and cell electrical impedance signature.

In some embodiments, the temperature-responsive material forms a layer on a surface of a device body. In some embodiments, the device body defines a first surface and a second surface that is located opposite the first surface, wherein a heater is disposed upon the first surface, and the temperature-responsive material forms a layer on the second surface. Thus, devices 10 of the present invention can be used in the practice of the methods of the invention for measuring a response of a population of living cells to an agent (e.g., living cells may be bound to temperature-responsive layer portion 32 of device 10 shown in FIGS. 1-3, and temperature-responsive layer portion 32 may then be contacted with an agent, and the response of the cells to the agent is measured).

In some embodiments, a multiplicity of different cell types are attached to the temperature-responsive material and are each contacted with the agent, wherein each different cell type is attached to a different portion of the temperature-responsive material. Thus, in those embodiments in which the temperature-responsive material forms a layer on a device surface, a multiplicity of different cell types can be attached to temperature-responsive layer 28, and they are each contacted with the agent. Each different cell type is attached to a different portion of temperature-responsive layer 28. For example, with reference to the embodiment of device 10 shown in FIGS. 4 and 5, six different cell types can be separately attached to first portion 50, second portion 52, third portion 54, fourth portion 58, fifth portion 60 and sixth portion 62 of temperature-responsive layer 28.

In a further aspect, the present invention provides methods for observing the binding of members of a binding pair, wherein the methods each include the steps of contacting a first member of a binding pair with a second member of a binding pair and observing the binding of the first member of the binding pair with the second member of the binding pair. In these methods the first member of the binding pair is attached to a temperature-responsive material that can exist in a first state that binds the first member of the binding pair, and can exist in a second state that binds substantially less of the first member of the binding pair than the first state. The temperature-responsive material is reversibly convertible to the first state from the second state in response to an effective amount of thermal energy, and the temperature-responsive material exists in the first state while the first member of the binding pair is contacted with the second member of the binding pair.

Members of binding pairs are molecules and/or living cells. Representative examples of binding pairs include an antibody and the antigen that is recognized and bound by the antibody (the antigen may itself be bound to a cell); an enzyme and its substrate (although it is understood that an enzyme may bind its substrate for a very short period of time); a receptor and its ligand; a cell-adhesive protein and a cell; and complementary nucleic acid molecules.

One member of a binding pair is attached to the temperature-responsive material. Either member of a binding pair can be attached to the temperature-responsive material. For example, if the binding pair is an antibody and the antigen that is recognized and bound by the antibody, either the antibody or the antigen can be attached to the temperature-responsive material, while the other member of the binding pair is not attached to the temperature-responsive material.

Examples of useful temperature-responsive materials are provided herein in connection with devices 10 of the invention. Binding of the first member of the binding pair with the second member of the binding pair can be observed by any useful means. For example, when the binding pair is an antibody and its antigen, and the antibody is attached to the temperature-responsive material, the antigen is typically labelled with a chemical moiety that produces a measurable signal so that binding of the antigen by the antibody can be observed. Examples of labels include fluorescent materials. Again by way of example, when the binding pair is an enzyme and its substrate, and the enzyme is attached to the temperature-responsive material, binding of the substrate by the enzyme can be observed by means of the formation of a colored product that is produced from the substrate by the enzyme. For example, Amplex Red reagent (from Molecular Probes, PO Box 22010, Eugene, Oreg. 97402-0469) is a fluorogenic substrate for the enzyme horseradish peroxidase. In the presence of horseradish peroxidase, the Amplex Red reagent reacts with a 1:1 stoichiometry with $H_2O_2$ to produce highly fluorescent resorufin.

In some embodiments, the temperature-responsive material forms a layer on a surface of a device body. In some embodiments, the device body defines a first surface and a second surface that is located opposite the first surface, wherein a heater is disposed upon the first surface, and the temperature-responsive material forms a layer on the second surface. Thus, devices 10 of the present invention can be used in the practice of the methods of the invention for observing the binding of members of a binding pair (e.g., a first member of a binding pair may be bound to temperature-responsive layer portion 32 of device 10 shown in FIGS. 1-3, and temperature-responsive layer portion 32 may then be contacted with the second member of the binding pair, and the binding of the members of the binding pair is observed).

In some embodiments, a multiplicity of different first members of a multiplicity of different binding pairs are attached to the temperature-responsive material and are contacted with a multiplicity of different second members of the multiplicity of different binding pairs, wherein each different first member of the multiplicity of different binding pairs is attached to a different portion of the temperature-responsive material. Thus, in those embodiments in which the temperature-responsive material forms a layer on a device surface, a multiplicity of different first members of a multiplicity of different binding pairs can be attached to temperature-responsive layer 28, and they are each contacted with a multiplicity of different second members of the multiplicity of different binding pairs. Each different first member of the multiplicity of different binding pairs is attached to a different portion of temperature-responsive layer 28. For example, with reference to the embodiment of device 10 shown in FIGS. 4 and 5, six different antibodies can be separately attached to first portion 50, second portion 52, third portion 54, fourth portion 58, fifth portion 60 and sixth portion 62 of temperature-responsive layer 28 (e.g., a first antibody is attached to first portion 50, a second antibody is attached to second portion 52, a third antibody is attached to third portion 54, a fourth antibody is attached to fourth portion 58, a fifth antibody is attached to fifth portion 60, and a sixth antibody is attached to sixth portion 62). Temperature-responsive layer 28 is then contacted with an aqueous solution including a first antigen recognized by the first antibody, a second antigen recognized by the second antibody, a third antigen recognized by the third antibody, a fourth antigen recognized by the fourth antibody, a fifth antigen recognized by the fifth antibody, and a sixth antigen recognized by the sixth antibody, wherein each of the antigens is labelled with a different fluorescent molecule that produces fluorescence that is distinguishable from the fluorescence produced by the other fluorescent molecules. Binding of the antigens to their respective antibodies is then observed.

The methods of this aspect of the invention are useful, for example, for performing immunoassays to observe, and optionally quantify, the binding of antibodies to their corresponding antigens in a fluid or tissue sample removed from a mammalian body (e.g., a human blood sample). The methods of this aspect of the invention are also useful, for example, for identifying novel substrates that are bound by a specific enzyme, or for identifying novel ligands that are bound by a specific receptor molecule.

The following examples merely illustrate the best mode now contemplated for practicing the invention, but should not be construed to limit the invention. All literature citations herein are expressly incorporated by reference.

EXAMPLE 1

This Example describes a representative method for making device 10 of the present invention.

In overview, the fabrication method uses a liftoff process for patterning metal films. A thin layer of photosensitive material (photoresist) was spun on a glass coverslip and patterned by photolithography. A thin metal film was then deposited using a thermal evaporation method. The glass coverslip was then soaked in acetone which dissolves the photoresist. The metal that was deposited directly on the glass coverslip remains, while the metal deposited on the photoresist detaches from the glass coverslip as the photoresist dissolves in the developing solution. This leaves the patterned metal layer that forms the heating elements, on the glass coverslip.

In detail, an initial cleaning procedure was performed to prepare a substrate for photolithography. The substrate, in this case a glass coverslip (VMR, Catalogue No. 48393 252) having dimensions of 24×60 mm, with a thickness of 0.18 mm, was soaked in acetone and ultrasonically agitated for ten minutes in the acetone. The glass coverslip was rinsed with isopropyl alcohol (IPA), and then blow-dried with nitrogen gas. After the initial cleaning procedure, the glass coverslip was heated for one minute on a hot plate at a temperature of 90° C. to drive off the adsorbed water on the surface.

The first step of the photolithography process immediately followed the dehydration bake. The glass coverslip was spin coated with a primer (P10) to assist the adhesion of photoresist to the glass. The spin rate was 500 rpm for five seconds, followed by 3000 rpm for thirty seconds. Positive photoresist (AZ1512, available from Clariant Corp.) was then spin coated to the primed glass at 500 rpm for five seconds, followed by 3000 rpm for thirty seconds.

The glass coverslip was then prebaked on a hot plate at 90° C. for three minutes to drive off the solvent in the photoresist, and to densify the resist after the spin coating. The glass coverslip was exposed to UV light for six seconds using an Oriel three-inch aligner through a mask, which has the array of designed heating elements. The design included narrow (30 μm) winding lines that formed the heating elements, and wide long lines with large contacting pads, which formed low resistance electrical contacts. After exposure the glass coverslip was soaked in a developer (MIF 300) for eight seconds. The developer solution only dissolved photoresist in the exposed areas. The glass coverslip was then rinsed with acetone and IPA, and blow dried with nitrogen gas.

To perform the metal deposition the glass coverslip was mounted on a silicon wafer (used as a carrier). A clean pipette was used to place a droplet of AZ1512 photoresist (acting as an adhesive) on top of a clean, three-inch silicon wafer. The photoresist was allowed to spread for ten seconds, and then the previously patterned glass coverslip was glued on top of the Az 1512 coated silicon wafer. The glass coverslip and silicon wafer were baked together on a hot plate for ten minutes at 100° C. to dry the photoresist and to ensure a strong bond between the glass coverslip and the carrying silicon wafer.

The next step involved metal depositions and was performed in a vacuum CVC thermal evaporation system. A 100

Angstrom (abbreviated as A) thick chromium film was first deposited. One thousand five hundred angstrom thick gold film was then deposited to set the heater resistance to around 100 Ohms. Chromium film was used to enhance adhesion of gold to the glass coverslip. 100 A chromium was again deposited, this time to enhance the gold adhesion to the passivation layer described in the next step. To complete the pattern transfer the glass coverslip and silicon wafer were soaked in acetone for 120 minutes with ultrasonic agitation for 30 seconds. In this step the acetone dissolves the photoresist and thus releases the glass from the three-inch silicon wafer and the metal films which were deposited on the photoresist. Metal films, which were deposited directly on the glass substrate, remain. The substrate is then rinsed with IPA and blow dried with nitrogen gas.

To complete the device microfabrication process, the glass substrate with the metallic heaters was coated with silicon nitride thin film that acts as a protection layer from environmental conditions such as high humidity. The contact area was covered with Scotch tape and the substrate was loaded into a Perkin Elmer Randex 2400 sputtering system. The substrate was sputtered with nitride for forty minutes at a background pressure before sputtering of less than 4 micro Torr. The tape was then removed and the glass coverslip was rinsed with acetone and IPA, and blow dried with nitrogen gas.

A temperature-responsive ppNIPAM layer was formed by plasma deposition using a plasma reactor connected to a 13.56 MHz radio-frequency power source. 2 g NIPAM monomer (Aldrich) was placed in a 100 mL glass flask. The flask was connected to a metering needle valve for monomer delivery rate control. The monomer flask was heated to 72-75° C. to vaporize NIPAM monomer. The monomer delivery line was maintained at 83° C. during the deposition process. After loading the substrates, the reactor was pumped to the low $10^{-3}$ Torr range. The deposition process included an 80W methane plasma deposition (adhesion promoting layer), followed by NIPAM plasma deposition with stepwise decreasing powers from 80W to 1W with a pressure of 100 mTorr for five minutes and ten minutes, respectively. The ppNIPAM-grafted surfaces were rinsed three times with cold deionized water to remove uncrosslinked molecules before further applications. The high power NIPAM plasma is to form strong crosslink with the substrate to prevent delamination. The low power NIPAM plasma is to preserve the side-chain functionalities that are believed to be the chemical origins of the temperature response.

EXAMPLE 2

This Example describes preferential binding of various types of animal cells to a temperature-responsive material.

Reagents and Materials: 97% N-isopropylacrylamid (NIPAM) was purchased from Aldrich (Milwaukee, Wis.) and used as received. The cell culture supplies were purchased from Gibco Invitrogen Corporation (Carlsbad, Calif.) and filtered though 0.2 μm filters before use. The cytotoxicity detection kit (Lactate Dehydrogenase (LDH) Assay Kit) was obtained from Roche Diagnostics Corporation (Indianapolis, Ind.). The 1,1'-dioctadecyl-3,3,3'3'-tetramethylindocarbocyanine (DiI)-conjugated acetylated low-density lipoprotein (DiI-Ac-LDL) was purchased from Biomedical Technologies (Stoughton, Mass.) and the FITC mouse monoclonal antibody conjugated to α-smooth muscle actin from Sigma (St. Louis, Mo.). Polyethylene terephthalate (PET) was purchased from Fisher Scientific Company (Houston, Tex.). Glass coverslips were obtained from VWR scientific (West Chester, Pa.).

Preparation of Temperature Responsive Layer: a temperature-responsive plasma polymerized NIPAM (ppNIPAM) layer was prepared by exposing 0.8 mm-by-0.8 mm poly (ethyleneterephthalate) (PET) substrate, tissue culture polystyrene dishes, or microheater chips to the vapor phase continuous NIPAM plasma as described in Example 1. The ppNIPAM-grafted surfaces were rinsed three times with cold deionized water to remove uncrosslinked molecules before use.

Cell Culture: bovine aortic endothelial cells (BAECs) (a generous gift from Dr. Cecilia Giachelli, University of Washington, Seattle, Wash.) were cultured in DMEM supplemented with 4.5 g/L glucose, 10% fetal bovine serum (FBS), 0.1 mM MEM non-essential amino acids, 1 mM MEM sodium pyruvate, 100 U/mL penicillin and 100 mg/mL streptomycin. Primary bovine aortic smooth muscle cells BASMCs (a generous gift from Dr. Cecilia Giachelli, University of Washington, Seattle, Wash.) were maintained in DMEM supplemented with 4.5 g/L glucose, 15% fetal bovine serum, 1 mM sodium pyruvate, 100 U/mL penicillin and 100 mg/mL streptomycin. HEK-293 cells were maintained in DMEM supplemented with 4.5 g/L glucose, 10% FBS, 100 U/mL penicillin and 100 mg/mL streptomycin. BAECs and HEK-293 cells were between passages 3 and 10. BAECs used in the study were between passage 7 and 15. Cell incubation was performed at 37° C. in a humidified atmosphere with 5% $CO_2$. The cells were dissociated from the culture flasks with trypsin/EDTA, washed with DPBS and resuspended in the respective culture media prior to the adhesion or patterning experiments.

Cell Adhesion, Proliferation and Detachment: plasma polymerized NIPAM (ppNIPAM)-coated PET and bare PET samples were fit into 48 well tissue culture polystyrene (TCPS) plates. 1 ml BAECs, BASMCs or HEK-293 cells in either serum-free or serum-containing DMEM were seeded on ppNIPAM coated PET, bare PET or TCPS at a cell density of $5 \times 10^4$/ml. The plates were cultured at either 37° C. or room temperature for 3 hours (BAECs and BASMCs) or 6 hours (HEK-293 cells). Half of the 37° C. incubated samples were transferred to room temperature and incubated for another 2 hours to study the cell response upon temperature drop. The cell morphology was observed under a phase contrast microscope (Nikon TE200 Inverted Microscope). The number of attached cells was determined using LDH assay, which is based on the principle of releasing the cytoplasmic enzyme LDH and measuring its activity in the supernatant. Briefly, the samples with adhered cells were washed twice with DPBS and cells were permeablized with 500 μl 1% triton-X100 for 30 minutes. 100 μl of the supernatant was transferred to a 96 well TCPS plate and mixed with the reaction solution for 30 minutes at room temperature. The absorbance of the solution was measured at 490 nm using a SpectraCount™ plate reader (Packard) and fitted onto a standard curve to determine the number of cells on each surface. The number of attached cells at each test condition was plotted with 6 replicas.

To test whether cells proliferate normally on the thermo-responsive polymer, ppNIPAM was directly coated on a 48 well TCPS plate. 1 ml cells were seeded at a cell density of $5 \times 10^4$ cells/ml in complete media. Cells cultured on untreated TCPS served as a control. The cells were cultured at 37° C. in a humidified atmosphere with 5% $CO_2$ and observed every day under a phase contrast microscope (Nikon TE200 Inverted Microscope). To test the response of the confluent cell sheet to temperature drop, the wells with confluent cell sheets were rinsed twice with DPBS and replenished with serum-free DMEM at room temperature. The plates were left at room temperature for 2 hours and observed.

Cell Patterning: A ppNIPAM-coated microheater chip was prepared as described in Example 1. A Teflon® chamber was built to hold the reaction solution only in contact with the side opposite to the metallic heating wires so that the heating wires were isolated from the electrolyte. To test the relationship between power input and surface temperature, a layer of thermochromic liquid crystal paint was applied on top of ppNIPAM on a test chip.

Cell patterning was performed using BAEC and BASMC from serum-free media. 400 µl BASMC suspended in serum-free DMEM was added to the chamber at a density of $2 \times 10^5$/ml to promote confluent cell adhesion. One heater was turned on with determined power input for 3 hours. The chip was rinsed three times with DPBS and 400 µl BAEC suspended in serum-free DEME was seeded at the same density with a second heater on for another three hours. The first heater was kept "on" during the whole process to prevent cell detachment.

Cell Staining and Fluorescence Microscopy: The cell-patterned chip was incubated with DMEM supplemented with 10% FBS and 4 µg/ml Dil-Ac-LDL at 37° C. for 4 hours to label BAECs. BAECs specifically take up the Dil-Ac-LDL and store it in the endosomal granula. The chip was washed with DPBS and the cells were fixed with 4% paraformaldehyde/0.1% Triton X-100 for 10 minutes. Then the chip was blocked with 1% BSA in DPBS for 30 minutes and reacted with an FITC-labeled-rabbit-polyclonal anti-bovine smooth muscle actin antibody at 1:100 dilution for 30 minutes at room temperature. The chip was observed under a fluorescence microscope (Nikon TE200 Inverted Microscope). The double stained images were superimposed with software (Metamorph Image).

Cell Adhesion: Cell adhesion on ppNIPAM coated PET, bare PET and TCPS were tested at either room temperature (below LCST) or 37° (above LCST). At 37° C., BAECs and BASMCs behaved similarly on the thermoresponsive and control surfaces after 3 hours incubation. Large number of cells were found to attach, adhere and spread on ppNIPAM, PET and TCPS from either serum-free or low serum-containing media (1% FBS for BAECs and 1.5% for BASMCs). However at room temperature, the effect of the ppNIPAM layer on cell behavior was immediately apparent. After 3 hours incubation at room temperature, adhesion of a great number of BAECs and BASMCs was again observed on TCPS and PET, while only few cells adhered on ppNIPAM at room temperature. Furthermore, when BAECs and BASMCs were first incubated at 37° C. for 3 hours and then cooled to room temperature for another 2 hours, spread cells on TCPS and PET had only minor morphological changes. In contrast, on ppNIPAM surfaces, most of the spread cells rounded up and detached from the surfaces after the temperature drop.

To quantify the number of adhered cells, the surfaces were rinsed with DPBS, and an LDH assay was carried out. In serum-free or low serum-containing media, the number of adhered BAECs and BASMCs on TCPS and PET were fairly constant, regardless of the incubation temperature and temperature drop. On ppNIPAM, however, number of cells was an order of magnitude lower when the incubation was carried out at room temperature than at 37° C. This was true of cells cultured in both serum-free and low serum-containing media. When 37° C. incubated samples were removed to room temperature to incubate for another 2 hours, 70% or more of the cells came off from ppNIAPM. When cell adhesion was tested with DMEM containing 10% FBS, the number of cells adhered at room temperature and 37° C. was not significantly different on ppNIPAM.

In serum-free or low serum-containing media, very few HEK-293 cells were found to adhere on any of the test surfaces. For this reason, subsequent cell adhesion experiments were carried out in DMEM supplemented with 10% FBS at 37° C. and room temperature for 6 hours. The number of HEK-293 cells adhered on TCPS and PET was 3 times lower at room temperature than at 37° C. from 10% serum media. On ppNIPAM, the difference increased to a factor of 10. When 37° C. incubated plates were brought to room temperature for 2 hours, the number of adhered cells on TCPS did not change significantly. In comparison, the number of adhered cells decreased by 68% and 50% respectively when ppNIPAM and PET were cooled from 37° C. to room temperature.

Cell Proliferation and Cell Sheet Detachment: BAECs, BASMCs and HEK-293 cells proliferated very similarly on TCPS, PET and ppNIPAM coated TCPS from complete media at 37° C. All three cell types reached confluence after 72 hours incubation on the three surfaces. The morphology of the cells was identical on ppNIPAM and control surfaces at confluence. When confluent HEK-293 and BAEC cells were transferred to room temperature, cell sheets were observed to come off immediately from ppNIPAM coated TCPS, but not from TCPS or bare PET, even after 12 hours at room temperature.

Cell Patterning: Based on the drastically different number of adhered cells on ppNIPAM at below and above the LCST, a microheater array chip was made that included a temperature-responsive ppNIPAM layer heated by three separate microheaters to spatially control the phase transition and cell adhesion on the ppNIPAM surface. The microheater array used in this work had three independent heaters. The resistance of each heating element was measured to be around 100 Ω. The chip was connected to a power source and contacted solution only on the side opposite to the metal layers. By monitoring with a layer of thermochromic liquid crystal paint, it was observed that 50 mW input power was required to heat the ppNIPAM surface to 35° C. -40° C. with 400 µl buffer in the chamber. The surface heated up almost instantaneously when the power was supplied, and the heating region was localized to around the heater with very little expansion over time. As the heating area was restricted to directly on top of the heating element, ppNIPAM transition to the non-fouling property was expected to be in the same localized region.

The cell patterning was first tested with a single type of cells. After seeding BAECs on ppNIPAM-coated microheater array chip for 3 hours with two heaters 'on', the cells were stained with Dil-Ac-LDL and observed under a fluorescence microscope. Ac-LDL is specifically uptaken by viable endothelial cells, so it gives information about both the viability and localization of the BAECs. Localized cell adhesion was observed, which associated with the heaters that were turned on. The pattern shape resembled the heating area observed using the thermochromic liquid crystal paint. These indicated that localized cell adhesion was driven by a temperature-induced polymer property change.

To pattern two types of cells, 400 µl BAECs and BASMCs were sequentially added into the Teflon® chamber with two different heaters being turned on in sequence. To prevent detachment of the first type of adhered cells, the first heater was left on during the whole process. BAECs and BASMCs were stained afterwards with molecules specific to cell types. Localized adhesion of the two types of cells was observed after staining. When a control experiment was performed with a microheater chip lacking the ppNIPAM coating, non-specific adhesion was observed all over the chip regardless of the heated or cold area.

EXAMPLE 3

This Example describes preferential binding of various types of proteins to an area of pNIPAM heated by a microheater.

Surface Preparation: ppNIPAM grafted surfaces were prepared by exposing 0.8 mm-by-0.8 mm PET or microheater chips to NIPAM glow discharge under continuous plasma, as described in Example 1. The ppNIPAM-grafted surfaces were rinsed three times with cold deionized water to remove uncrosslinked monomers before use.

Protein Adsorption: Protein adsorption was performed using $I^{125}$-labeled proteins at room temperature (23° C.), or at 37° C., or through temperature cycles using citrate and phosphate buffered saline containing sodium iodide and sodium azide (CPBSzI, pH=7.4). I-125 labeled human fibrinogen (Enzyme Research), BSA (Sigma) and goat IgG (Sigma) were prepared using the iodine monochloride technique (D. Williams, Techniques of Biocompatibility Testing Volume II, CRC Press, Boca Raton 1986, pp. 184-212). Radiolabeled proteins were added to unlabeled protein solutions to obtain a specific activity of 5 cpm/ng and final protein concentration of 0.03, 0.1 and 0.05 mg/ml for fibrinogen, BSA and IgG adsorption, respectively. Amounts of adsorbed proteins were calculated from the retained radioactivity (corrected for background) and the specific activity of the protein solution.

Fabrication of Microheater Chips and Patterning of Proteins: A ppNIPAM coated microheater chip was prepared as described in Example 1. The size of the heating elements used in this study was 1 mm by 1 mm. The resistance of the heating elements was around 100Ω, ppNIPAM was deposited as the functional layer on the side opposite to the heaters. To isolate the heating wires from the electrolytes and reduce the consumption of expensive reagents, a Teflon® chamber was built to hold the solutions in contact with only the ppNIPAM-coated side. A layer of thermochromic liquid crystal paint was applied on top of the heaters to monitor the surface temperature at different heating powers. Protein patterning was performed by first adding 400 μl 0.05 mg/ml FITC-anti-BSA into the chamber, turning on one heater with 50 mW power supply and allowing protein to adsorb for 0.5 hours. The chip was rinsed 3 times with CPBS, followed by TRITC-goat-IgG adsorption in the same manner.

Fluorescence Labeling of Proteins and Fluorescence Microscopy: Goat IgG and anti-BSA antibody were labeled with FITC and TRITC respectively before patterning using the FITC Protein Labeling Kit (Molecular Probes). Then the chip was blocked with 1% BSA in DPBS for 30 minutes and reacted with a FITC-labeled-rabbit-polyclonal anti-bovine smooth muscle actin antibody (Sigma) at 1:100 dilution for 30 minutes at room temperature. The protein patterned chips were observed under a fluorescence microscope (Nikon TE200 Inverted Microscope). The double stained images were superimposed with software (Metamorph image).

Results of Protein Binding Studies: To test the temperature response of the ppNIPAM films, the 2 hour protein adsorption on ppNIPAM coated PET was measured using $^{125}$I-labeled bovine serum albumin (BSA), IgG and fibrinogen at both room temperature (below the LCST) and 37° C. (above the LCST). As shown in Table 1, at room temperature less than 25 ng/cm$^2$ of BSA, IgG or fibrinogen adsorbed on the surfaces. At 37° C., the amount of protein adsorbed on ppNIPAM increased by eleven, temperature. The amount of protein adsorbed on ppNIPAM at 37° C. was a little lower than that on the control PET surfaces, suggesting submonolayer protein coverage on ppNIPAM. Increase in protein adsorption as a function of temperature was noticed exclusively on the thermo-responsive ppNIPAM surfaces, but not on the control PET surfaces. There were 5 replicates for each data point shown in Table 1.

TABLE 1

|  | Fibrinogen | IgG | BSA |
| --- | --- | --- | --- |
| ppNIPAM (R.T.) | 18 ± 5 | 22 ± 5 | 17 ± 9 |
| ppNIPAM (37° C.) | 185 ± 9 | 183 ± 31 | 191 ± 18 |
| PET (R.T.) | 315 ± 15 | 450 ± 57 | 189 ± 22 |
| PET (37° C.) | 269 ± 10 | 347 ± 49 | 266 ± 17 |

To further assess the protein adsorption on ppNIPAM, samples incubated at room temperature and at 37° C. were switched to 37° C. and room temperature, respectively, and allowed to incubate for another 2 hours. The low adsorptive surfaces at room temperature became protein retentive by incubating at 37° C., while the proteins adsorbed at 37° C. did not detach from ppNIPAM when the incubation temperature dropped. These experiments indicated that protein adsorption on ppNIPAM is an irreversible process over the time frame of several hours.

Protein Patterning Results: Protein patterning on the ppNIPAM coated microheater array was performed using FITC-labeled goat IgG and TRITC-labeled anti-BSA. The two proteins were added in the chamber sequentially with two different heaters turned on at 50 mW. Each protein was allowed to adsorb for 30 minutes. Preferential adsorption of each protein was expected to localize directly on top of the corresponding working heater. Site-specific adsorption of the two proteins was observed under a fluorescent microscope.

EXAMPLE 4

This Example describes the use of the present invention to discover drug candidates for treatment of diabetes based upon the known effect of the glucagon-like peptide 1 (GLP-1) to increase insulin secretion in pancreatic beta-islet cells (see, Miguel, J. C. et al. *Biochemical Pharmacology* 65:283-292, 2003).

A sample reservoir contains rat BRIN BD11 cells, cultured in RPMI 1640 media containing 10% fetal calf serum, 100 U/ML penicillin, 0.1 mg/mL streptomycin and 11.1 mM glucose. All these media components are purchased from GIBCO Life Technologies. A micro-fluidic stream of cells from the sample reservoir is loaded into an array chamber, followed by raising the temperature to 37° C. only in the array zones where it is desired for cells to attach. Following adsorption of the cells, unbound cells are washed off the rest of the array with cell-free RPMI media. A second set of different cells, such as the human pancreatic beta-islet cell line MIN6 are thermally localized to different zones in the array. Each of these cell types includes the GLP-1 receptor.

The mixed cell array is treated in sequential fashion with candidate agonists, or antagonists, of the GLP-1 receptor. The candidate molecules (hereafter referred to as drugs) are contained in separate sample reservoirs in the microfluidic stream. The drugs can be dissolved in either serum-free RPMI medium or, in order to assess the bioavailability of the drugs to the cells due to serum protein binding, RMPI supplemented with 10% fetal bovine serum. Following incubation with the drug for the appropriate time, the cells are cultured at 37° C., followed by analysis of insulin expression either by staining the entire array with anti-insulin antibodies to detect a decrease in insulin secretion, or by hybridization of the entire array with DNA probes for insulin RNA expression. By these means, the effect of the drug on the different cell types provides critical information pertaining to the specificity of the drug. This specificity can be ascertained further by inclusion of non-GLP responsive insulin secreting cells, which can be created by silencing the GLP-1 receptor in the cell lines through genetic engineering, or pre-incubation with GLP-1 receptor antibodies. Of great benefit to these types of studies is the use of very small micro-heater arrays (e.g., 50 square microns) that localize single cells. Typically, cellular drug-sensitivity assays are confounded by having, in a population of clonally selected identical cells, varying sensitivity to the drug. This variance makes it difficult to compare precisely the potency and metabolism of a given compound. Separating the population into single cells, affords a significant enhancement to the power of the analysis.

By using the thermally-controlled cellular array, in this fashion, the system enables the precise detection of more potent and selective synthetic low-molecular weight synthetic drugs agonists of GLP-1 that promote insulin secretion in diabetics.

EXAMPLE 5

This Example describes the use of the present invention to discover, or optimize, drug candidates that specifically inhibit the interaction of FOXO1 and PPARGC1 transcription factors that are believed to be involved in the development of type II diabetes.

Many diseases have aberrant signal transduction pathways that contribute to altered gene expression and development of pathologic states in tissues and cells. It is common for these signaling pathways to involve the binding of protein pairs in the cascade of events that ultimately changes the profile of gene expression in the cells of diseased tissue. Of particular interest are the interactions of sets of transcription factors that, upon differential degrees of phosphorylation, form specific combinations of separate proteins into assemblies that can bind differently to exposed regions of DNA and control gene expression. This aberrant signaling is at the root of many multifactorial diseases, such as diabetes.

The release of glucose from glycogen stores in the liver is normally suppressed by insulin but is inappropriately activated in diabetes (Puigserver, P. et al. *Nature* 423(6939): 550-5 (2003)). It has been proposed that two intracellular proteins, the fork-head transcription factor (FOX01) and the peroxisome proliferative activated receptor-gamma co-activator 1 (PPARGC1) cooperate to promote a pronounced insulin-controlled production of glucose in the liver. Suppression of this interaction would correct a major defect in diabetes.

To discover or optimize drug candidates capable of specifically inhibiting the interaction of FOXO1 and PPARGC1, an array is created by applying a stream of solution of Dulbecco's phosphate buffered saline (DPBS) containing either FOXO1 or PPARGC1, in a pattern produced via control of the temperature in each zone of the array. Following washing of the array with protein-free DPBS, to remove unbound protein, the other partner of the protein pair is introduced in the presence or absence of the drug candidate. If the drug is capable of inhibiting the binding of FOXO1 to PPARGC1, then the second protein (FOXO1 or PPARGC1) will not bind to the thermally-pre-adsorbed partner. Following incubation, the entire array is washed and immunostained with FOXO1 and PPARGC1 antibodies to detect the specific binding of the proteins. Control zones in the array are created to be devoid of protein, or to contain a different protein that does not bind FOXO1 or PPARGC1. In this way the specificity and integrity of protein-pair binding is determined.

This approach can be extended to include transcription factor complexes that involve more than two proteins to assemble into a fully functional molecular assembly. The thermally-controlled array is especially useful to assemble these complexes under precise control one protein at a time. Thus, drug candidates can be screened that inhibit the precise three-dimensional structure that is only present at the time of assembly. Such studies of protein dynamics are difficult to perform in solution. They are made possible by the ability of the thermally-controlled array system to isolate temporally and spatially the assembly of multi-component protein complexes.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A device for binding cells or molecules, wherein the device comprises:
   (a) a body defining a first surface and a second surface that is located opposite to the first surface;
   (b) multiple heaters disposed upon the first surface, wherein some or all of the heaters are independently controllable; and
   (c) a temperature-responsive layer disposed upon the second surface, wherein the temperature-responsive layer is deposited by plasma deposition at a first high deposition power and at least one second low deposition power, and comprises a temperature-responsive material having a first layer that crosslinks and adheres to the second surface at the first high deposition power and at least one second layer that forms at the at least one second low deposition power that can exist in a first state that binds molecules or living cells, and can exist in a second state that binds substantially less molecules or living cells than the first state, and wherein the temperature-responsive material is reversibly convertible to the first state from the second state in response to an effective amount of thermal energy.

2. The device of claim 1 wherein the body consists essentially of a material selected from the group consisting of glass, silicon, mica, quartz, sapphire, and poly(ethyleneterephthalate).

3. The device of claim 1 wherein the body has a thickness in the range of from 0.0001 mm to 2 mm.

4. The device of claim 1 wherein the first surface and the second surface each have an area in the range of from 1 mm$^2$ to 5 cm$^2$.

5. The device of claim 1 wherein the device comprises a longest dimension in the range of from 1.0 mm to 5.0 cm.

6. The device of claim 1 wherein the first surface and the second surface are both rectangular.

7. The device of claim 1 wherein the first surface and the second surface are both square.

8. The device of claim 1 wherein the temperature-responsive material is selected from the group consisting of poly(N-isopropylacrylamide), poly(N,N-dimethylacrylamide), poly(ethylacrylamide), poly(N-ethylmethacrylamide), poly[N-(3-ethoxypropyl)acrylamide], poly[N-(2-hydroxypropyl) methacrylamide], poly(N-vinylisobutyramide), poly(N-vinylacetamide), a copolymer of methoxy poly(ethylene glycol) and poly(propylene fumarate), a vinyl ether of ethylene glycol, hydroxypropylcellulose, ethyl hydroxyethyl cellulose, methyl cellulose, poly(vinyl methyl ether), butyl vinyl ether, polyglycidol, acryloyt-L-proline methyl ester, a vinyl pyrrolidone and vinyl acetate copolymer, a copolymer of N-acryloyl-N'-alkyl piperazine and methyl methacrylate, poly(methyl 2-propionamidoacrylate), poly(acrylic acid), poly(acrylamide-co-butyl methacrylate), poly(organophosphazenes), poly(2-ethyl-2-oxazoline), gelatin, poly(N-vinylcaprolactam), elastin, elastin mimetic polypeptide, 2,4,6-trimethylpyridine and poly(N-vinylpyrrolidone).

9. The device of claim 1 wherein the temperature-responsive material consists essentially of poly (N-isopropylacrylamide).

10. The device of claim 1 wherein at least one living cell is attached to a portion of the temperature-responsive layer.

11. The device of claim 1 wherein protein molecules are attached to a portion of the temperature-responsive layer.

12. The device of claim 11 wherein the protein molecules are antibody molecules.

13. The device of claim 1 wherein the multiple heaters comprise a first population of heaters and a second population of heaters, and the temperature-responsive layer comprises a first population of portions, located opposite the first population of heaters, and a second population of portions, located opposite the second population of heaters, wherein a first type of living cell is attached to the first population of portions, and a second, different, type of living cell is attached to the second population of portions.

14. The device of claim 1 wherein the multiple heaters comprise a first population of heaters and a second population of heaters, and the temperature-responsive layer comprises a first population of portions, located opposite the first population of heaters, and a second population of portions, located opposite the second population of heaters, wherein a first type of protein molecules is attached to the first population of portions, and a second, different, type of protein molecules is attached to the second population of portions.

15. A method for binding molecules or living cells to a temperature-responsive material, wherein the method comprises the steps of contacting a temperature-responsive material with a population of molecules or a population of living cells, wherein:

(a) the temperature-responsive material can exist in a first state that binds molecules or living cells, and can exist in a second state that binds substantially less molecules or living cells than the first state, and wherein the temperature-responsive material is reversibly convertible to the first state from the second state in response to an effective amount of thermal energy;

(b) the temperature-responsive material exists in the first state when the temperature-responsive material is contacted with the population of molecules or living cells, thereby effecting binding of the molecules or living cells to the temperature-responsive material; (c) the temperature-responsive material is deposited by plasma deposition at a first high deposition power and at least one second low deposition power, and has a first layer that crosslinks and adheres to a surface at the first high deposition power and at least one second layer that forms at the at least one second low deposition power.

16. The method of claim 15 wherein molecules are bound to the temperature-responsive material.

17. The method of claim 16 wherein the molecules are proteins.

18. The method of claim 17 wherein the proteins are antibodies.

19. The method of claim 15 wherein living cells are bound to the temperature-responsive material.

20. The method of claim 15 wherein the temperature-responsive material is selected from the group consisting of poly(N-isopropylacrylamide), poly(N,N-dimethylacrylamide), poly(ethylacrylamide), poly(N-ethylmethacrylamide), poly[N-(3-ethoxypropyl)acrylamide], poly[N-(2-hydroxypropyl)methacrylamide], poly(N-vinylisobutyramide), poly(N-vinylacetamide), a copolymer of methoxy poly(ethylene glycol) and poly(propylene fumarate), a vinyl ether of ethylene glycol, hydroxypropylcellulose, ethyl hydroxyethyl cellulose, methyl cellulose, poly(vinyl methyl ether), butyl vinyl ether, polyglycidol, acryloyl-L-proline methyl ester, a vinyl pyrrolidone and vinyl acetate copolymer, a copolymer of N-acryloyl-N'-alkyl piperazine and methyl methacrylate, poly(methyl 2-propionamidoacrylate), poly(acrylic acid), poly(acrylamid-co-butyl methacrylate), poly(organophosphazenes), poly(2-ethyl-2-oxazoline), gelatin, poly(N-vinylcaprolactam), elastin, elastin mimetic polypeptide, 2,4,6-trimethylpyridine and poly(N-vinylpyrrolidone).

21. The method of claim 15 wherein the temperature-responsive material consists essentially of poly (N-isopropylacrylamide).

22. The method of claim 15 wherein the temperature-responsive material is heated to a temperature between 32° C. and 40° C. so that the temperature-responsive material exists in the first state.

23. The method of claim 15 wherein the temperature-responsive material forms a layer on a surface of a device body.

24. The method of claim 23 wherein the device body defines a first surface and a second surface that is located opposite the first surface, wherein a heater is disposed upon the first surface, the temperature-responsive material forms a layer on the second surface, and the heater heats the temperature-responsive material so that the temperature-responsive material exists in the first state and binds the molecules or living cells.

25. A method for binding more than one type of molecule or more than one type of living cell to a temperature-responsive material, wherein the method comprises the steps of:

(a) contacting a temperature-responsive material with a first type of molecules or a first type of living cells, wherein the temperature-responsive material is attached to a device body wherein the device body defines a first surface and a second surface that is located opposite the first surface, wherein a first population of heaters and a second population of heaters are disposed upon the first surface, and wherein the temperature-responsive layer is deposited by plasma deposition at a first high deposition power and at least one second low deposition power, and comprises a temperature-responsive material having a first layer that crosslinks and adheres to the second surface at the first high deposition power and at least one second layer that forms at the at least one second low deposition that can exist in a first state that binds molecules or living cells, and can exist in a second state that binds substantially less molecules or living cells than the first state, and wherein the temperature-responsive material is reversibly convertible to the first state from the second state in response to an effective amount of thermal energy wherein the temperature-responsive material forms a temperature-responsive layer on the second surface;

(b) activating the first population of heaters to heat a first population of temperature-responsive layer portions, located on the second surface opposite the first population of heaters, so that the first type of molecules or the first type of living cells binds to the first population of temperature-responsive layer portions, said activation occurring before or during the contacting of the temperature-responsive material with the first type of molecules or the first type of living cells;

(c) removing any of the first type of molecules or the first type of living cells that are not bound to the first population of temperature-responsive layer portions;

(d) contacting the temperature-responsive material with a second type of molecules or a second type of living cells;

(e) activating the second population of heaters to heat a second population of temperature-responsive layer portions, located on the second surface opposite the second population of heaters, so that the second type of molecules or the second type of living cells binds to the second population of temperature-responsive layer portions, said activation occurring before or during the contacting of the temperature-responsive material with the second type of molecules or the second type of living cells; and (f) removing any of the second type of molecules or the second type of living cells that are not bound to the second population of temperature-responsive layer portions.

26. The method of claim 25 wherein a first type of protein is bound to the first population of temperature-responsive layer portions, and a second type of protein is bound to the second population of temperature-responsive layer portions.

27. The method of claim 26 wherein the first type of protein and the second type of protein are both antibodies.

28. The method of claim 25 wherein a first type of living cell is bound to the first population of temperature-responsive layer portions, and a second type of living cell is bound to the second population of temperature-responsive layer portions.

29. The method of claim 25 wherein a first type of living cell is bound to the first population of temperature-responsive layer portions, and a second type of living cell is bound to the second population of temperature-responsive layer portions, wherein the first population of heaters remains activated while the second population of heaters are activated.

30. A method for measuring a response of a population of living cells to an agent, wherein the method comprises the steps of contacting a population of living cells with an agent and measuring a response of the living cells to the agent, wherein the living cells are attached to a temperature-responsive material that can exist in a first state that binds living cells, and can exist in a second state that binds substantially less living cells than the first state, wherein the temperature-responsive material is deposited by plasma deposition at a first high deposition power and at least one second low deposition power, and has a first layer that crosslinks and adheres to a surface at the first high deposition power and at least one second layer that forms at the at least one second low deposition power, wherein the temperature-responsive material is reversibly convertible to the first state from the second state in response to an effective amount of thermal energy, and wherein the temperature-responsive material exists in the first state while the living cells are contacted with the agent.

31. The method of claim 30 wherein the temperature-responsive material is selected from the group consisting of poly(N-isopropylacrylamide), poly(N,N- dimethylacrylamide), poly(ethylacrylamide),poly(N-ethylmethacrylamide), poly[N-(3-ethoxypropyl)acrylamide], poly[N-(2-hydroxypropyl)methacrylamide], poly(N-vinylisobutyramide), poly(N-vinylacetamide), a copolymer of methoxy poly(ethylene glycol) and poly(propylene fumarate), a vinyl ether of ethylene glycol, hydroxypropylcellulose, ethyl hydroxyethyl cellulose, methyl cellulose, poly(vinyl methyl ether), butyl vinyl ether, polyglycidol, acryloyl-L-proline methyl ester, a vinyl pyrrolidone and vinyl acetate copolymer, a copolymer of N-acryloyl-N'-alkyl piperazine and methyt methacrylate, poly(methyl 2-propionamidoacrylate), poly(acrylic acid), poly(acrytamid-co-butyl methacrylate), poly(organophosphazenes), poly(2-ethyl-2-oxazoline), gelatin, poly(N-vinylcaprolactam), elastin, elastin mimetic polypeptide, 2,4,6-trimethylpyridine and poly(N-vinylpyrrolidone).

32. The method of claim 30 wherein the temperature-responsive material consists essentially of poly (N-isopropylacrylamide).

33. The method of claim 30 wherein the temperature-responsive material forms a layer on a surface of a device body.

34. The method of claim 33 wherein the device body defines a first surface and a second surface that is located opposite the first surface, wherein a heater is disposed upon the first surface, and the temperature-responsive material forms a layer on the second surface.

35. The method of claim 34 wherein a multiplicity of different cell types are attached to the temperature-responsive layer and are each contacted with the agent, wherein each different cell type is attached to a different portion of the temperature-responsive layer.

36. The method of claim 30 wherein a multiplicity of different cell types are attached to the temperature-responsive material and are each contacted with the agent, wherein each different cell type is attached to a different portion of the temperature-responsive material.

37. A method for observing the binding of members of a binding pair, wherein the method comprises the steps of contacting a first member of a binding pair with a second member of a binding pair and observing the binding of the first member of the binding pair with the second member of the binding pair, wherein the first member of the binding pair is attached to a temperature-responsive material that can exist in a first state that binds the first member of the binding pair, and can exist in a second state that binds substantially less first member of the binding pair than the first state, wherein the temperature-responsive material is deposited by plasma deposition at a first high deposition power and at least one second low deposition power, and has a first layer that crosslinks and adheres to a surface at the first high deposition power and at least one second layer that forms at the at least one second low deposition power, wherein the temperature-responsive material is reversibly convertible to the first state from the second state in response to an effective amount of thermal energy, and wherein the temperature-responsive material exists in the first state while the first member of the binding pair is contacted with the second member of the binding pair.

38. The method of claim 37 wherein the first member of the binding pair is an antibody, and the second member of the binding pair is an antigen to which the antibody binds.

39. The method of claim 37 wherein the first member of the binding pair is an antigen, and the second member of the binding pair is an antibody that binds to the antigen.

40. The method of claim 37 wherein the first member of the binding pair is an enzyme, and the second member of the binding pair is a substrate for the enzyme.

41. The method of claim 37 wherein the first member of the binding pair is a substrate for an enzyme, and the second member of the binding pair is the enzyme that utilizes the substrate.

42. The method of claim 37 wherein the temperature-responsive material is selected from the group consisting of poly(N-isopropylacrylamide), poly(N,N- dimethylacrylamide), poly(ethylacrylamide), poly(N-ethylmethacrylamide), poly[N-(3-ethoxypropyl)acrylamide], poly[N-(2-hydroxypropyl)methacrylamide], poly(N-vinylisobutyramide), poly(N-vinylacetamide), a copolymer of methoxy poly(ethylene glycol) and poly(propylene fumarate), a vinyl ether of ethylene glycol, hydroxypropylcellulose, ethyl hydroxyethyl cellulose, methyl cellulose, poly(vinyl methyl ether), butyl vinyl ether, polyglycidol, acryloyl-L-proline methyl ester, a vinyl pyrrolidone and vinyl acetate copolymer, a copolymer of N-acryloyl-N'-alkyl piperazine and methyt methacrylate, poly(methyl 2-propionamidoacrylate), poly(acrylic acid), poly(acrytamid-co-butyl methacrylate), poly(organophosphazenes), poly(2-ethyl-2-oxazoline), gelatin, poly(N-vinylcaprolactam), elastin, elastin mimetic polypeptide, 2,4,6-trimethylpyridine and poly(N-vinylpyrrolidone).

43. The method of claim 42 wherein the temperarature-responsive material consist essentially of poly(N-isopropylacrylamide).

44. The method of claim 37 wherein the temperature-responsive material forms a layer on a surface of a device body.

45. The method of claim 44 wherein the device body defines a first surface and a second surface that is located opposite the first surface, wherein a heater is disposed upon the first surface, and the temperature-responsive material forms a layer on the second surface.

46. The method of claim 37 wherein a multiplicity of different first members of a multiplicity of different binding pairs are attached to the temperature-responsive material and are contacted with a multiplicity of different second members of the multiplicity of different binding pairs, wherein each different first member of the multiplicity of different binding pairs is attached to a different portion of the temperature-responsive material.

* * * * *

UNITED STATES PATENT AND TRADEMARK OFFICE
CERTIFICATE OF CORRECTION

PATENT NO. : 7,442,515 B2
APPLICATION NO. : 10/630235
DATED : October 28, 2008
INVENTOR(S) : B. D. Ratner et al.

It is certified that error appears in the above-identified patent and that said Letters Patent is hereby corrected as shown below:

| COLUMN | LINE | ERROR |
|---|---|---|
| 24 (Claim 8, lines 6-7) | 65-66 | "poly(N-vinylacctamide)," should read --poly(N-vinylacetamide),-- |
| 25 (Claim 8, line 11) | 3 | "acryloyt-L-proline methyl ester," should read --acryloyl-L-proline methyl ester,-- |
| 25 (Claim 15, line 17) | 54 | after "material;" insert --and;-- and subindent the clause "(c) the temperature-responsive material . . . power." |
| 26 (Claim 25, line 11) | 48 | after "surface," insert --wherein the temperature-responsive material forms a temperature-responsive layer on the second surface-- |
| 26 (Claim 25, lines 24-26) | 61-63 | after "thermal energy" delete --wherein the temperature-responsive material forms a temperature-responsive layer on the second surface-- |

UNITED STATES PATENT AND TRADEMARK OFFICE
CERTIFICATE OF CORRECTION

PATENT NO. : 7,442,515 B2
APPLICATION NO. : 10/630235
DATED : October 28, 2008
INVENTOR(S) : B. D. Ratner et al.

It is certified that error appears in the above-identified patent and that said Letters Patent is hereby corrected as shown below:

| COLUMN | LINE | ERROR |
|---|---|---|
| 27 (Claim 31, line 4) | 62 | after "poly(ethylacrylamide)," insert a space |
| 28 (Claim 31, line 13) | 4 | "methyt" should read --methyl-- |
| 29 (Claim 42, line 13) | 9 | "methyt" should read --methyl-- |

Signed and Sealed this

Twenty-first Day of July, 2009

JOHN DOLL
*Acting Director of the United States Patent and Trademark Office*